United States Patent
Hang et al.

(10) Patent No.: US 12,297,451 B1
(45) Date of Patent: May 13, 2025

(54) CELL CULTURE MEDIUM

(71) Applicant: Regeneron Pharmaceuticals, Inc., Tarrytown, NY (US)

(72) Inventors: Ta-Chun Hang, Morristown, NJ (US); John Zhao, North Arlington, NJ (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 467 days.

(21) Appl. No.: 17/077,134

(22) Filed: Oct. 22, 2020

Related U.S. Application Data

(60) Provisional application No. 62/925,800, filed on Oct. 25, 2019.

(51) Int. Cl.
*C12N 5/00* (2006.01)

(52) U.S. Cl.
CPC ........ *C12N 5/0018* (2013.01); *C12N 2500/05* (2013.01); *C12N 2500/14* (2013.01); *C12N 2500/32* (2013.01); *C12N 2500/50* (2013.01); *C12N 2500/60* (2013.01); *C12N 2501/148* (2013.01); *C12N 2501/15* (2013.01); *C12N 2501/22* (2013.01); *C12N 2501/2302* (2013.01); *C12N 2501/24* (2013.01); *C12N 2501/39* (2013.01)

(58) Field of Classification Search
CPC .............. C12N 5/0018; C12N 2500/14; C12N 2500/32; C12N 2501/148; C12N 2501/15; C12N 2501/22; C12N 2501/2302; C12N 2501/24; C12N 2501/39
See application file for complete search history.

(56) References Cited

U.S. PATENT DOCUMENTS

| | | |
|---|---|---|
| 4,072,565 A | 2/1978 | Weiss et al. |
| RE30,985 E | 6/1982 | Cartaya |
| 4,560,655 A | 12/1985 | Baker |
| 4,615,977 A | 10/1986 | Hasegawa et al. |
| 4,657,866 A | 4/1987 | Kumar |
| 4,786,599 A | 11/1988 | Chessebeuf et al. |
| 5,063,157 A | 11/1991 | Stockinger |
| 5,122,469 A | 6/1992 | Mather et al. |
| 5,342,777 A | 8/1994 | Cole et al. |
| 5,426,699 A | 6/1995 | Wunderlich et al. |
| 5,460,964 A | 10/1995 | McGlave et al. |
| 5,529,920 A | 6/1996 | Cole et al. |
| 5,610,279 A | 3/1997 | Brockhaus et al. |
| 5,635,387 A | 6/1997 | Fei et al. |
| 5,677,136 A | 10/1997 | Simmons et al. |
| 5,705,364 A | 1/1998 | Etcheverry et al. |
| 5,716,827 A | 2/1998 | Tsukamoto et al. |
| 5,728,581 A | 3/1998 | Schwartz et al. |
| 5,750,397 A | 5/1998 | Tsukamoto et al. |
| 5,759,793 A | 6/1998 | Schwartz et al. |
| 5,811,299 A | 9/1998 | Renner et al. |
| 5,856,179 A | 1/1999 | Chen et al. |
| 5,976,833 A | 11/1999 | Furukawa et al. |
| 6,043,092 A | 3/2000 | Block |
| 6,048,728 A | 4/2000 | Inlow et al. |
| 6,087,123 A | 7/2000 | Wissler et al. |
| 6,146,847 A | 11/2000 | Goffe et al. |
| 6,180,401 B1 | 1/2001 | Chen et al. |
| 6,528,286 B1 | 3/2003 | Ryll |
| 6,589,759 B1 | 7/2003 | Loscalzo et al. |
| 6,924,124 B1 | 8/2005 | Singh |
| 6,927,004 B2 | 8/2005 | Eurlings et al. |
| 7,070,959 B1 | 7/2006 | Papadopoulos et al. |
| 7,087,411 B2 | 8/2006 | Daly et al. |
| 7,105,348 B2 | 9/2006 | Murphy et al. |
| 7,279,159 B2 | 10/2007 | Daly et al. |
| 7,294,484 B2 | 11/2007 | Drapeau et al. |
| 7,303,694 B2 | 12/2007 | Murphy et al. |
| 7,429,491 B2 | 9/2008 | Luan et al. |
| 7,435,553 B2 | 10/2008 | Fandl et al. |
| 7,455,988 B2 | 11/2008 | Fandl et al. |
| 7,582,298 B2 | 9/2009 | Stevens et al. |
| 7,666,416 B2 | 2/2010 | Etcheverry et al. |
| 7,750,138 B2 | 7/2010 | Fang et al. |
| 7,771,997 B2 | 8/2010 | Chen et al. |
| 7,879,984 B2 | 2/2011 | Martin et al. |
| 7,951,577 B2 | 5/2011 | Murphy et al. |
| 8,021,881 B2 | 9/2011 | Reiter et al. |
| 8,043,617 B2 | 10/2011 | Stevens et al. |
| 8,062,640 B2 | 11/2011 | Sleeman et al. |
| 8,216,575 B2 | 7/2012 | Yu |
| 8,313,926 B2 | 11/2012 | Grillberger et al. |

(Continued)

FOREIGN PATENT DOCUMENTS

| | | |
|---|---|---|
| CA | 2045208 C | 11/2003 |
| CA | 2091636 C | 2/2004 |

(Continued)

OTHER PUBLICATIONS

O2375 L-ornithine monohydrochloride. Datasheet [online]. Sigma, 2023 [retrieved on Apr. 22, 2023]. Retrieved from the Internet: <https://www.sigmaaldrich.com/US/en/search/o2375?focus=products&page=1&perpage=30&sort=relevance&term=o2375&type=product>. (Year: 2023).*

McAdams, Todd., The characterization of extracellular pH and medium osmolality as important parameters in the culture of human hematopoietic cells. Dissertation Northwestern University Evanston, IL Dec. 1997 (Year: 1997).*

Dotti., et al., Design and development of therapies using chimeric antigen receptor-expressing T cells. Immunology Review, vol. 257, No. 1 (Jan. 2014) doi:10.1111/imr.12131 (Year: 2014).*

Casero Jr., et al., "Polyamine metabolism and cancer: treatments, challenges and opportunities," Nat Rev Cancer. Nov. 2018; 18(11): 681-695.

De Nadal et al., "Osmostress-induced gene expression—a model to understand how stress-activated protein kinases (SAPKs) regulate transcription," FEBS Journal 282 (2015) 3275-3285.

(Continued)

*Primary Examiner* — Kara D Johnson
(74) *Attorney, Agent, or Firm* — McCarter & English, LLP; Marcie B. Clarke; Dylan M. Blumenthal

(57) ABSTRACT

The present disclosure provides improved cell culture media for maintaining and expanding immune effector cell and hematopoietic stem or progenitor cell populations.

17 Claims, 6 Drawing Sheets

(56) References Cited

U.S. PATENT DOCUMENTS

| | | |
|---|---|---|
| 8,426,202 B2 | 4/2013 | Cayli |
| 8,440,408 B2 | 5/2013 | Grillberger et al. |
| 8,637,312 B2 | 1/2014 | Kruger et al. |
| 8,735,095 B2 | 5/2014 | Martin et al. |
| 8,871,209 B2 | 10/2014 | Stitt et al. |
| 8,945,559 B2 | 2/2015 | Dix et al. |
| 9,018,356 B2 | 4/2015 | Sleeman et al. |
| 9,045,536 B2 | 6/2015 | Merchant et al. |
| 9,079,948 B2 | 7/2015 | Orengo et al. |
| 9,127,265 B2 | 9/2015 | Grillberger et al. |
| 9,150,645 B2 | 10/2015 | Subramanian et al. |
| 9,173,880 B2 | 11/2015 | Dix et al. |
| 9,181,572 B2 | 11/2015 | Subramanian et al. |
| 9,217,168 B2 | 12/2015 | Prentice |
| 9,228,014 B2 | 1/2016 | Classon et al. |
| 9,260,515 B2 | 2/2016 | Stitt et al. |
| 9,265,827 B2 | 2/2016 | Wiegand et al. |
| 9,266,949 B2 | 2/2016 | Ramasubramanyan et al. |
| 9,302,015 B2 | 4/2016 | Papadopoulos et al. |
| 9,353,176 B2 | 5/2016 | MacDonald et al. |
| 9,359,434 B2 | 6/2016 | Subramanian et al. |
| 9,402,898 B2 | 8/2016 | Walsh et al. |
| 9,428,727 B2 | 8/2016 | Leist et al. |
| 9,447,431 B2 | 9/2016 | Thess et al. |
| 9,499,616 B2 | 11/2016 | Subramanian et al. |
| 9,633,810 B2 | 4/2017 | Iwanabe et al. |
| 9,644,181 B2 | 5/2017 | Matsuyama et al. |
| 9,663,810 B2 | 5/2017 | Prentice |
| 9,714,411 B2 | 7/2017 | Grillberger et al. |
| 9,758,568 B2 | 9/2017 | Grillberger et al. |
| 9,809,796 B2 | 11/2017 | Gillberger et al. |
| 10,415,016 B2 | 9/2019 | Ostertag et al. |
| 10,513,686 B2 | 12/2019 | Ostertag et al. |
| 10,927,342 B2 | 2/2021 | Johnson et al. |
| 11,332,771 B2 | 5/2022 | Oshodi et al. |
| 11,802,269 B2 | 10/2023 | Ostertag et al. |
| 2006/0094104 A1 | 5/2006 | Grillberger et al. |
| 2006/0094113 A1 | 5/2006 | Epstein et al. |
| 2007/0212770 A1 | 9/2007 | Grillberger et al. |
| 2007/0212778 A1 | 9/2007 | Bramke et al. |
| 2009/0137416 A1 | 5/2009 | Fandl et al. |
| 2009/0162901 A1 | 6/2009 | Chen et al. |
| 2010/0120093 A1 | 5/2010 | von Fircks et al. |
| 2010/0227819 A1 | 9/2010 | Hernandez et al. |
| 2010/0285533 A1 | 11/2010 | Kruger et al. |
| 2010/0304436 A1 | 12/2010 | Chen et al. |
| 2010/0331527 A1 | 12/2010 | Davis et al. |
| 2011/0229933 A1 | 9/2011 | Krishnan et al. |
| 2012/0034674 A1 | 2/2012 | Grillberger et al. |
| 2012/0264170 A1 | 10/2012 | Merchant et al. |
| 2012/0308549 A1 | 12/2012 | Fogh et al. |
| 2013/0084605 A1 | 4/2013 | Zhou et al. |
| 2013/0130316 A1 | 5/2013 | Joosten et al. |
| 2013/0224855 A1 | 8/2013 | Gupta et al. |
| 2013/0295613 A1 | 11/2013 | Kishishita et al. |
| 2013/0344535 A1 | 12/2013 | Mundt et al. |
| 2014/0044730 A1 | 2/2014 | Yancopoulos et al. |
| 2014/0088295 A1 | 3/2014 | Smith et al. |
| 2014/0154726 A1 | 6/2014 | Yang et al. |
| 2014/0271642 A1 | 9/2014 | Murphy et al. |
| 2014/0271653 A1 | 9/2014 | Gurnett-Bander et al. |
| 2014/0271658 A1 | 9/2014 | Murphy et al. |
| 2014/0271681 A1 | 9/2014 | Martin et al. |
| 2014/0273095 A1 | 9/2014 | Oshodi et al. |
| 2014/0274912 A1 | 9/2014 | Prentice |
| 2015/0104867 A1 | 4/2015 | Grillberger et al. |
| 2015/0203579 A1 | 7/2015 | Papadopoulos et al. |
| 2015/0203580 A1 | 7/2015 | Papadopoulos et al. |
| 2015/0216795 A1 | 8/2015 | Assadourian et al. |
| 2015/0259423 A1 | 9/2015 | Kirshner et al. |
| 2015/0266966 A1 | 9/2015 | Smith et al. |
| 2015/0313194 A1 | 11/2015 | Hu et al. |
| 2015/0329826 A1 | 11/2015 | Van Den Bos et al. |
| 2015/0337029 A1 | 11/2015 | Kyratsous et al. |
| 2015/0337045 A1 | 11/2015 | Okamoto et al. |
| 2016/0002594 A1 | 1/2016 | Yang et al. |
| 2016/0017029 A1 | 1/2016 | Walsh et al. |
| 2016/0024502 A1 | 1/2016 | Streicher et al. |
| 2016/0075778 A1 | 3/2016 | Okamoto et al. |
| 2016/0076068 A1 | 3/2016 | Engel et al. |
| 2016/0083689 A1 | 3/2016 | Grillberger et al. |
| 2016/0215040 A1 | 7/2016 | Kyratsous et al. |
| 2016/0237400 A1 | 8/2016 | Xian |
| 2016/0333385 A1 | 11/2016 | Kang et al. |
| 2017/0107553 A1 | 4/2017 | Kottakota et al. |
| 2017/0198251 A1 | 7/2017 | Elhofy et al. |
| 2017/0305999 A1 | 10/2017 | Leber et al. |
| 2018/0223249 A1 | 8/2018 | Johnson et al. |
| 2018/0298078 A1 | 10/2018 | Park et al. |
| 2018/0346881 A1 | 12/2018 | Clemens et al. |
| 2019/0010531 A1 | 1/2019 | Chen et al. |
| 2019/0092836 A1 | 3/2019 | Leister et al. |
| 2019/0352598 A1* | 11/2019 | Sabatini ............... C12N 5/0018 |
| 2020/0131554 A1 | 4/2020 | Chen et al. |
| 2020/0149081 A1 | 5/2020 | Oshodi et al. |
| 2020/0157492 A1 | 5/2020 | Johnson et al. |
| 2020/0255880 A1 | 8/2020 | Chen et al. |
| 2021/0332402 A1 | 10/2021 | Oshodi et al. |
| 2021/0340560 A1 | 11/2021 | Clarke |
| 2021/0388407 A1 | 12/2021 | Chen et al. |
| 2021/0388408 A1 | 12/2021 | Chen et al. |
| 2022/0228187 A1 | 7/2022 | Oshodi et al. |

FOREIGN PATENT DOCUMENTS

| | | |
|---|---|---|
| CN | 1241573 A | 1/2000 |
| CN | 1367258 A | 9/2002 |
| CN | 101065480 A | 10/2007 |
| CN | 101220347 A | 7/2008 |
| CN | 101360820 A | 2/2009 |
| CN | 101603026 A | 12/2009 |
| CN | 102093978 A | 6/2011 |
| CN | 102224239 A | 10/2011 |
| CN | 102317440 A | 1/2012 |
| DE | 266710 C | 10/2012 |
| EP | 0073657 A1 | 3/1983 |
| EP | 0183070 A2 | 6/1986 |
| EP | 0244234 A2 | 11/1987 |
| EP | 0307247 A2 | 3/1989 |
| EP | 0308936 A2 | 3/1989 |
| EP | 0402226 A1 | 12/1990 |
| EP | 0591605 A2 | 4/1994 |
| EP | 1321515 A1 | 6/2003 |
| EP | 2921554 A1 | 9/2015 |
| EP | 2971040 A1 | 1/2016 |
| JP | 7-507446 A | 8/1995 |
| JP | 2013-208104 A | 10/2013 |
| RU | 2192884 C2 | 11/2002 |
| WO | 1987/000195 A1 | 1/1987 |
| WO | 1990/003430 A1 | 4/1990 |
| WO | 1990/013646 A1 | 11/1990 |
| WO | 1991/000360 A1 | 1/1991 |
| WO | 1991/010741 A1 | 7/1991 |
| WO | 1992/009298 A1 | 6/1992 |
| WO | 1992/009690 A2 | 6/1992 |
| WO | 1992/020373 A1 | 11/1992 |
| WO | 1993/006213 A1 | 4/1993 |
| WO | 1993/008829 A1 | 5/1993 |
| WO | 1993/016185 A2 | 8/1993 |
| WO | 1993/018143 A1 | 9/1993 |
| WO | 1994/004690 A1 | 3/1994 |
| WO | 1994/011026 A2 | 5/1994 |
| WO | 1996/007754 A1 | 3/1996 |
| WO | 1996/027011 A1 | 9/1996 |
| WO | 1996/033735 A1 | 10/1996 |
| WO | 1996/034096 A1 | 10/1996 |
| WO | 1998/024893 A2 | 6/1998 |
| WO | 1998/045411 A1 | 10/1998 |
| WO | 1998/059035 A1 | 12/1998 |
| WO | 1999/035255 A2 | 7/1999 |
| WO | 1999/064578 A1 | 12/1999 |
| WO | 2002/069733 A1 | 9/2002 |
| WO | 2002/101019 A2 | 12/2002 |
| WO | 2005/028626 A2 | 3/2005 |

(56) References Cited

FOREIGN PATENT DOCUMENTS

| WO | 2006/044908 A2 | 4/2006 |
|---|---|---|
| WO | 2006/089232 A2 | 8/2006 |
| WO | 2006/116034 A1 | 11/2006 |
| WO | 2006/116369 A2 | 11/2006 |
| WO | 2007/050498 A2 | 5/2007 |
| WO | 2007/077217 A2 | 7/2007 |
| WO | 2007/146123 A2 | 12/2007 |
| WO | 2008/063892 A2 | 5/2008 |
| WO | 2008/154014 A2 | 12/2008 |
| WO | 2009/020144 A1 | 2/2009 |
| WO | 2011/008770 A2 | 1/2011 |
| WO | 2011/019619 A1 | 2/2011 |
| WO | 2011/079004 A1 | 6/2011 |
| WO | 2012/091124 A1 | 7/2012 |
| WO | 2013/184809 A1 | 12/2013 |
| WO | 2014/020160 A1 | 2/2014 |
| WO | 2014/029772 A1 | 2/2014 |
| WO | 2014/058025 A1 | 4/2014 |
| WO | 2014/144198 A1 | 9/2014 |
| WO | 2014/145098 A1 | 9/2014 |
| WO | 2015/105609 A1 | 7/2015 |
| WO | 2015/105926 A1 | 7/2015 |
| WO | 2015/184009 A1 | 12/2015 |
| WO | 2019/010191 A1 | 1/2019 |
| WO | 2020/075319 A1 | 4/2020 |
| WO | 2023/077026 A1 | 5/2023 |

OTHER PUBLICATIONS

Droge et al., "Suppression of Cytotoxic T Lymphocyte Activation by L-Ornithine," The Journal of Immunology, vol. 134, No. 5, May 1985, 6 pages.

Ebina, "Combinatorial Pathway Modulation toward Ex Vivo Maintenance and Propagation of Hematopoietic Stem Cells," Doctoral dissertation, Harvard University, Graduate School of Arts & Sciences, Mar. 2016, 173.

Geiger et al., "L-Arginine Modulates T Cell Metabolism and Enhances Survival and Anti-tumor Activity," Cell. Oct. 20, 2016; 167(3): 829-842.

Han et al., "A Map kinase targeted by endotoxin and hyperosmolarity in mammalian cells," Science (1994) 365 (5173): 808-11.

Hesterberg et al., "Role of Polyamines in Immune Cell Functions," Med. Sci. 2018, 6, 22.

Legraverend et al., "Interleukin-2 Induces a Rapid Increase in Ornithine Decarboxylase mRNA in a Cloned Murine T Lymphocytic Cell Line," Experimental Cell Research 181 (1989) 273-281.

Messaoud et al., "Basic Properties of the p38 Signaling Pathway in Response to Hyperosmotic Shock," PLOS One, Sep. 3, 2015, 15 pages.

Soda et al., "Spermine, a Natural Polyamine, Suppresses LFA-1 Expression on Human Lymphocyte," J Immunol 2005; 175:237-245.

Zhao et al., "CDK inhibitor p57Kip2 is downregulated by Akt during HER2-mediated tumorigenicity," Cell Cycle 12:6, 935-943; Mar. 15, 2013.

GenBank Accession No. NP_001274118, ornithine decarboxylase isoform 1[*Homo sapiens*]. 3 pages, Mar. 17, 2024.

Graham et al., Characteristics of a human cell line transformed by DNA from human adenovirus type 5. J Gen Virol. Jul. 1977;36(1):59-74.

Gram et al., In vitro selection and affinity maturation of antibodies from a naive combinatorial immunoglobulin library. Proc Natl Acad Sci U S A. Apr. 15, 1992;89(8):3576-80.

Griffiths et al., Human anti-self antibodies with high specificity from phage display libraries. Embo J. Feb. 1993;12(2):725-34.

Gruber et al., Efficient tumor cell lysis mediated by a bispecific single chain antibody expressed in *Escherichia coli*. J Immunol. Jun. 1, 1994;152(11):5368-74.

Guirard et al., Effect of Polyamine Structure on Growth Stimulation and Spermine and Spermidine Content of Lactic Acid Bacteria. J Bacteriol. Jul. 1964;88(1):72-80.

Gupta, Correlating composition and functionality of soy protein hydrolysates used in animal cell cultures. Thesis submitted in fulfilment of the requirements for the degree of doctor at Wageningen University. 132 pages, Jul. 3, 2015.

Gurer et al., Antioxidant effect of taurine against lead-induced oxidative stress. Arch Environ Contam Toxicol. Nov. 2001;41(4):397-402.

Guss et al., Structure of the IgG-binding regions of streptococcal protein G. Embo J. Jul. 1986;5(7):1567-75.

Ham et al., Media and growth requirements. Methods Enzymol. 1979;58:44-93.

Ham, Clonal Growth of Mammalian Cells in a Chemically Defined, Synthetic Medium. Proc Natl Acad Sci U S A. Feb. 1965;53(2):288-93.

Han et al., Effects of polyamines on apoptosis induced by simulated ischemia/reperfusion injury in cultured neonatal rat cardiomyocytes. Cell Biol Int. Nov. 2007;31(11):1345-52.

Hawel et al., Selective putrescine export is regulated by insulin and ornithine in Reuber H35 hepatoma cells. Biochim Biophys Acta. May 26, 1994;1222(1):15-26.

Hawkins et al., Selection of phage antibodies by binding affinity. Mimicking affinity maturation. J Mol Biol. Aug. 5, 1992;226(3):889-96.

Hernandez-Benitez et al., Taurine stimulates proliferation of mice embryonic cultured neural progenitor cells. J Neurosci Res. Jun. 2010; 88(8):1673-81.

Hogrefe et al., A bacteriophage lambda vector for the cloning and expression of immunoglobulin Fab fragments on the surface of filamentous phage. Gene. Jun. 15, 1993; 128(1):119-26.

Hollenbaugh et al., Construction of immunoglobulin fusion proteins. Curr Protoc Immunol. May 2002;Chapter 10: Unit 10.19A, 11 pages.

Holliger et al., "Diabodies": small bivalent and bispecific antibody fragments. Proc Natl Acad Sci U S A. Jul. 15, 1993;90(14):6444-8.

Holmes et al., Serum fractionation and the effects of bovine serum fractions on human cells grown in a chemically defined medium. J Biophys Biochem Cytol. Jul. 1961;10(3):389-401.

Holtta et al., Polyamine dependence of Chinese hamster ovary cells in serum-free culture is due to deficient arginase activity. Biochim Biophys Acta. Dec. 30, 1982;721(4):321-7.

Hongo et al., Development and characterization of murine monoclonal antibodies to the latency-associated peptide of transforming growth factor beta 1. Hybridoma. Jun. 1995;14(3):253-60.

Hoogenboom et al., By-passing immunisation. Human antibodies from synthetic repertoires of germline VH gene segments rearranged in vitro. J Mol Biol. Sep. 20, 1992;227(2):381-8.

Hoogenboom et al., Multi-subunit proteins on the surface of filamentous phage: methodologies for displaying antibody (Fab) heavy and light chains. Nucleic Acids Res. Aug. 11, 1991;19(15):4133-7.

Hoogenboom, Overview of Antibody Phage-Display Technology and Its Applications. Methods in Molecular Biology, vol. 178: Antibody Phage Display, Methods and Protocols. P.M. O'Brien (Ed.), Humana Press, Inc., Totowa. 37 pages, (2002).

Huang et al., Maximizing productivity of CHO cell-based fed-batch culture using chemically defined media conditions and typical manufacturing equipment. Biotechnol Prog. Sep.-Oct. 2010;26(5):1400-10.

Hudson et al., Engineered antibodies. Nat Med. Jan. 2003;9(1):129-34.

Igarashi et al., Modulation of cellular function by polyamines. Int J Biochem Cell Biol. Jan. 2010;42(1):39-51.

Jakobovits et al., Analysis of homozygous mutant chimeric mice: deletion of the immunoglobulin heavy-chain joining region blocks B-cell development and antibody production. Proc Natl Acad Sci U S A. Mar. 15, 1993;90(6):2551-5.

Jakobovits et al., Germ-line transmission and expression of a human-derived yeast artificial chromosome. Nature. Mar. 18, 1993;362(6417):255-8.

Jensen et al., Selective inhibition of fibroblasts by spermine in primary cultures of normal human skin epithelial cells. In Vitro. Oct. 1982; 18(10):867-71.

Jones et al., Proteinase mutants of Saccharomyces cerevisiae. Genetics. Jan. 1977;85(1):23-33.

(56) References Cited

OTHER PUBLICATIONS

Jones et al., Rapid PCR-cloning of full-length mouse immunoglobulin variable regions. Biotechnology (N Y). Jan. 1991;9(1):88-9.
Jones et al., Replacing the complementarity-determining regions in a human antibody with those from a mouse. Nature. May 29-Jun. 4, 1986;321(6069):522-5.
Jong et al., Effect of beta-alanine treatment on mitochondrial taurine level and 5-taurinomethyluridine content. J Biomed Sci. Aug. 24, 2010;17 Suppl 1(Suppl 1):S25, 7 pages.
Jong et al., Mechanism underlying the antioxidant activity of taurine: prevention of mitochondrial oxidant production. Amino Acids. Jun. 2012;42(6):2223-32.
Jong et al., Role of mitochondrial permeability transition in taurine deficiency-induced apoptosis. Exp Clin Cardiol. 2011 Winter;16(4):125-8.
Kanemura et al., In Vitro Screening of Exogenous Factors for Human Neural Stem/Progenitor Cell Proliferation Using Measurement of Total ATP Content in Viable Cells. Cell Transplant. Oct. 2005;14(9):673-682.
Kang et al., Metabolic markers associated with high mannose glycan levels of therapeutic recombinant monoclonal antibodies. J Biotechnol. Jun. 10, 2015;203:22-31.
Kaufman et al., Synthesis, processing, and secretion of recombinant human factor VIII expressed in mammalian cells. J Biol Chem. May 5, 1988;263(13):6352-62.
Kaufman, Selection and coamplification of heterologous genes in mammalian cells. Methods Enzymol. 1990;185:537-66.
Kaufman, Use of recombinant DNA technology for engineering mammalian cells to produce proteins. Bioprocess Technol. 1990;10:15-69.
Kelley, Industrialization of mAb production technology: the bioprocessing industry at a crossroads. MAbs. Sep.-Oct. 2009;1(5):443-52.
Kim et al., Development of serum-free medium supplemented with hydrolysates for the production of therapeutic antibodies in CHO cell cultures using design of experiments. Appl Microbiol Biotechnol. Jun. 2009;83(4):639-48.
Kipriyanov et al., Recombinant single-chain Fv fragments carrying C-terminal cysteine residues: production of bivalent and biotinylated miniantibodies. Mol Immunol. Oct. 1994;31(14):1047-58.
Kipriyanov et al., Single-chain antibody streptavidin fusions: tetrameric bifunctional scFv-complexes with biotin binding activity and enhanced affinity to antigen. Hum Antibodies Hybridomas. 1995;6(3):93-101.
Kohler et al., Continuous cultures of fused cells secreting antibody of predefined specificity. Nature. Aug. 7, 1975;256 (5517):495-7.
Korang et al., Levels of taurine, amino acids and related compounds in plasma, vena cava, aorta and heart of rats after taurine administration. Pharmacology. Apr. 1996;52(4):263-70.
Kostelny et al., Formation of a bispecific antibody by the use of leucine zippers. J Immunol. Mar. 1, 1992;148 (5):1547-53.
Kou et al., Increasing the Productivity of TNFR-Fc in GS-CHO Cells at Reduced Culture Temperatures. Biotechnology and Bioprocess Engineering. 2011;16:136-143.
Kozbor et al., A human hybrid myeloma for production of human monoclonal antibodies. J Immunol. Dec. 1984;133(6):3001-5.
Allen et al., Inhibition of lymphocyte proliferation by polyamines requires ruminant-plasma polyamine oxidase. Eur J Biochem. Dec. 1979; 102(1):153-8.
Altamirano et al., Analysis of CHO cells metabolic redistribution in a glutamate-based defined medium in continuous culture. Biotechnol Prog. Nov.-Dec. 2001; 17(6):1032-41.
Altamirano et al., Specific nutrient supplementation of defined serum-free medium for the improvement of CHO cells growth and t-PA production. Electronic Journal of Biotechnology. Jan. 15, 2006;9(1):61-67.
Ashkenazi et al., Protection against endotoxic shock by a tumor necrosis factor receptor immunoadhesin. Proc Natl Acad Sci U S A. Dec. 1, 1991;88(23):10535-9.
Barbas et al., Assembly of combinatorial antibody libraries on phage surfaces: the gene III site. Proc Natl Acad Sci U S A. Sep. 15, 1991;88(18):7978-82.

Barbas et al., Semisynthetic combinatorial antibody libraries: a chemical solution to the diversity problem. Proc Natl Acad Sci U S A. May 15, 1992;89(10):4457-61.
Barnes et al., Methods for growth of cultured cells in serum-free medium. Anal Biochem. Mar. 1, 1980;102(2):255-70.
Bass et al., Hormone phage: an enrichment method for variant proteins with altered binding properties. Proteins. 1990;8(4):309-14.
Bettger et al., Rapid clonal growth and serial passage of human diploid fibroblasts in a lipid-enriched synthetic medium supplemented with epidermal growth factor, insulin, and dexamethasone. Proc Natl Acad Sci U S A. Sep. 1981;78(9):5588-92.
Boerner et al., Production of antigen-specific human monoclonal antibodies from in vitro-primed human splenocytes. J Immunol. Jul. 1, 1991;147(1):86-95.
Bokati et al., Corrosion inhibition of copper, mild steel and galvanically coupled copper-mild steel in artificial sea water in presence of 1H-benzotriazole, sodium molybdate and sodium phosphte. Corrosion Science. 2017;126:272-285.
Branca et al., Inhibition of ornithine decarboxylase of Hela cells by diamines and polyamines. Effect on cell proliferation. Biochem J. Mar. 15, 1980;186(3):925-31.
Brasel et al., Hematologic effects of flt3 ligand in vivo in mice. Blood. Sep. 15, 1996;88(6):2004-12.
Brennan et al., Preparation of bispecific antibodies by chemical recombination of monoclonal immunoglobulin G1 fragments. Science. Jul. 5, 1985;229(4708):81-3.
Brodeur et al., Mouse-Human Myeloma Partners for the Production of Heterohybridomas. Production of Heterohybridmas. Chapter 4, pp. 51-63, (1987).
Bruggemann et al., Designer mice: the production of human antibody repertoires in transgenic animals. Year Immunol. 1993;7:33-40.
Byrn et al., Biological properties of a CD4 immunoadhesin. Nature. Apr. 12, 1990;344(6267):667-70.
Carter et al., High level Escherichia coli expression and production of a bivalent humanized antibody fragment. Biotechnology (N Y). Feb. 1992;10(2):163-7.
Carter et al., Humanization of an anti-p185HER2 antibody for human cancer therapy. Proc Natl Acad Sci U S A. May 15, 1992;89(10):4285-9.
CAS Registry No. 107-35-7, 2 pages, (2020).
Casero et al., Targeting polyamine metabolism and function in cancer and other hyperproliferative diseases. Nat Rev Drug Discov. May 2007;6(5):373-90.
Charlton et al., Expression and isolation of recombinant antibody fragments in E. coli. Methods Mol Biol. 2004;248:245-54.
Chen et al., A serum-free medium for hybridoma cell culture. Cytotechnology. 1993;11(3):169-74.
Chothia et al., Canonical structures for the hypervariable regions of immunoglobulins. J Mol Biol. Aug. 20, 1987;196(4):901-17.
Clackson et al., Making antibody fragments using phage display libraries. Nature. Aug. 15, 1991;352(6336):624-8.
Cozzi et al., Taurine and ellagic acid: two differently-acting natural antioxidants. Environ Mol Mutagen. 1995;26(3):248-54.
Daugherty et al., Formulation and delivery issues for monoclonal antibody therapeutics. Adv Drug Deliv Rev. Aug. 7, 2006;58(5-6):686-706.
Davidson et al., The nucleoprotein content of fibroblasts growing in vitro: 2. The effect of tissue extracts. Biochem J. 1945;39(2):188-99.
Declerck et al., Importance of manufacturing consistency of the glycosylated monoclonal antibody adalimumab (Humira) and potential impact on the clinical use of biosimilars. GaBI J. 2016;5(2):70-73.
Duchosal et al., Immunization of hu-PBL-SCID mice and the rescue of human monoclonal Fab fragments through combinatorial libraries. Nature. Jan. 16, 1992;355(6357):258-62.
Dulbecco, Production of Plaques in Monolayer Tissue Cultures by Single Particles of an Animal Virus. Proc Natl Acad Sci U S A. Aug. 1952;38(8):747-52.
Eagle, Nutrition needs of mammalian cells in tissue culture. Science. Sep. 16, 1955;122(3168):501-14.

(56) References Cited

OTHER PUBLICATIONS

Embleton et al., In-cell PCR from mRNA: amplifying and linking the rearranged immunoglobulin heavy and light chain V-genes within single cells. Nucleic Acids Res. Aug. 11, 1992;20(15):3831-7.
Eremeeva et al., Effects of the antioxidant alpha-lipoic acid on human umbilical vein endothelial cells infected with Rickettsia rickettsii. Infect Immun. May 1998;66(5):2290-9.
European Pharmacopoeia 7.0, N-Acetyltyrosine. pp. 1320, 1322, 1323, (2008).
Even et al., Serum-free hybridoma culture: ethical, scientific and safety considerations. Trends Biotechnol. Mar. 2006;24(3):105-8.
Fan et al., Amino acid and glucose metabolism in fed-batch CHO cell culture affects antibody production and glycosylation. Biotechnol Bioeng. Mar. 2015; 112(3):521-35.
Fellouse et al., Synthetic antibodies from a four-amino-acid code: a dominant role for tyrosine in antigen recognition. Proc Natl Acad Sci U S A. Aug. 24, 2004; 101(34):12467-72.
Fishwild et al., High-avidity human IgG kappa monoclonal antibodies from a novel strain of minilocus transgenic mice. Nat Biotechnol. Jul. 1996; 14(7):845-51.
Fleer et al., Stable multicopy vectors for high-level secretion of recombinant human serum albumin by Kluyveromyces yeasts. Biotechnology (N Y). Oct. 1991;9(10):968-75.
Franek et al., Plant protein hydrolysates: preparation of defined peptide fractions promoting growth and production in animal cells cultures. Biotechnol Prog. Sep.-Oct. 2000;16(5):688-92.
Froud et al., Polyamine Enhanced Product Expression from Transformed and Recombinant Cell Lines. Production of Biological from Animal Cells in Culture. pp. 107-109, (1991).
Fusi et al., Effects of putrescine, cadaverine, spermine, spermidine and beta-phenylethylamine on cultured bovine mammary epithelial cells. Ital J Amin Sci. 2008;7:131-140.
Gahl et al., Reversal by aminoguanidine of the inhibition of proliferation of human fibroblasts by spermidine and spermine. Chem Biol Interact. Jul. 1978;22(1):91-8.
Gerngross, Advances in the production of human therapeutic proteins in yeasts and filamentous fungi. Nat Biotechnol. Nov. 2004;22(11):1409-14.
Goding, Production of Monoclonal Antibodies. Monoclonal Antibodies: Principles and Practice. Academic Press, Orlando. Chapter 3, pp. 56-97, (1984).
Google Scholar, "a trap molecule." Retrieved online at: <https://scholar.google.com/scholar?hl=en&as_std=0%22a+trap+molecule.> 2 pages, Jul. 23, 2020.
Google, Nutrient Mixture F-12 Ham Formulation. SIGMA-ALDRICH, Cell Culture. Retrieved online at: <https://www.sigmaaldrich.com/life-science/cell-culture/learning-center/media-formulations/f-12-ham.printview.html.> 7 pages, retrieved Apr. 12, 2019.
Wikipedia, Putrescine. Retrieved online at: <https://en.wikipedia.org/wiki/Putrescine.> 5 pages, (2020).
Wikipedia, Sarilumab. Retrieved online at: <https://en.wikipedia.org/wiki/Sarilumab.> 3 pages, (2020).
Williams et al., Cloning and sequencing of human immunoglobulin V lambda gene segments. Eur J Immunol. Jul. 1993;23(7):1456-61.
Williams et al., Isolation and long-term cell culture of epithelial-like cells from rat liver. Exp Cell Res. Nov. 1971;69(1):106-12.
Winter et al., Making antibodies by phage display technology. Annu Rev Immunol. 1994; 12:433-55.
Wood et al., High level synthesis of immunoglobulins in Chinese hamster ovary cells. J Immunol. Nov. 1, 1990;145(9):3011-6.
Yanagita et al., Taurine reduces the secretion of apolipoprotein B100 and lipids in HepG2 cells. Lipids Health Dis. Oct. 17, 2008;7:38, 6 pages.
Yaniv, Enhancing elements for activation of eukaryotic promoters. Nature. May 6, 1982;297(5861):17-8.
Yazaki et al., Expression of recombinant antibodies in mammalian cell lines. Methods Mol Biol. 2004;248:255-68.
Chinese Office Action for Application No. 201480023485.4, dated Apr. 18, 2017, 13 pages.
European Application No. 14723561.8, Experimental report—Impact of Ornithine and Putrescine Addition on MB02 Culture, submitted by the opponent on Jul. 16, 2020 in Opposition Against European Patent No. 2970876, 23 pages, (2020).
European Office Action for Application No. 18172141.6, dated Jun. 29, 2018, 11 pages.
International Search Report and Written Opinion for Application No. PCT/US2014/029772, dated Jul. 24, 2014, 9 pages.
International Search Report and Written Opinion for Application No. PCT/US2016/045403, dated Oct. 4, 2016, 10 pages.
International Preliminary Report on Patentability for Application No. PCT/US2016/045403, dated Feb. 15, 2018, 8 pages.
International Search Report and Written Opinion for Application No. PCT/US2018/040734, dated Oct. 18, 2018, 18 pages.
Kucharzewska et al., Ornithine decarboxylase and extracellular polyamines regulate microvascular sprouting and actin cytoskeleton dynamics in endothelial cells. Exp Cell Res. Oct. 1, 2010;316(16):2683-91.
Kumar et al., Differential protein expression following low temperature culture of suspension CHO-K1 cells. BMC Biotechnol. Apr. 22, 2008;8:42, 13 pages.
Kyriakopoulos et al., Comparative analysis of amino acid metabolism and transport in CHO variants with different levels of productivity. J Biotechnol. Dec. 2013;168(4):543-51.
Lalonde et al., Therapeutic glycoprotein production in mammalian cells. J Biotechnol. Jun. 10, 2017;251:128-140.
Lee et al., Bivalent antibody phage display mimics natural immunoglobulin. J Immunol Methods. Jan. 2004;284(1-2):119-32.
Lee et al., High-affinity human antibodies from phage-displayed synthetic Fab libraries with a single framework scaffold. J Mol Biol. Jul. 23, 2004;340(5):1073-93.
Lelong et al., In vitro taurine uptake into cell culture influenced by using media with or without CO2. J Pharmacol Toxicol Methods. Jun. 1998;39(4):211-20.
Leon et al., Protective function of taurine in glutamate-induced apoptosis in cultured neurons. J Neurosci Res. Apr. 2009;87(5):1185-94.
Leung et al., A Method for Random Mutagenesis of a Defined DNA Segment Using a Modified Polymerase Chain Reaction. Technique JMCMB. 1989; 1:11-15.
Li et al., Cell culture processes for monoclonal antibody production. MAbs. Sep.-Oct. 2010;2(5):466-79.
Li et al., Optimization of humanized IgGs in glycoengineered Pichia pastoris. Nat Biotechnol. Feb. 2006;24(2):210-5.
Li et al., Screening soy hydrolysates for the production of a recombinant therapeutic protein in commercial cell line by combined approach of near-infrared spectroscopy and chemometrics. Appl Microbiol Biotechnol. Mar. 2013;97 (6):2653-60.
Lindmark et al., Binding of immunoglobulins to protein A and immunoglobulin levels in mammalian sera. J Immunol Methods. Aug. 12, 1983;62(1): 1-13.
Lonberg et al., Antigen-specific human antibodies from mice comprising four distinct genetic modifications. Nature. Apr. 28, 1994;368(6474):856-9.
Lonberg et al., Human antibodies from transgenic mice. Int Rev Immunol. 1995; 13(1):65-93.
Marks et al., By-passing immunization. Human antibodies from V-gene libraries displayed on phage. J Mol Biol. Dec. 5, 1991;222(3):581-97.
Marks et al., By-passing immunization: building high affinity human antibodies by chain shuffling. Biotechnology (N Y). Jul. 1992; 10(7):779-83.
Mather et al., Culture of testicular cells in hormone-supplemented serum-free medium. Ann N Y Acad Sci. 1982;383:44-68.
Mather, Establishment and characterization of two distinct mouse testicular epithelial cell lines. Biol Reprod. Aug. 1980;23(1): 243-52.
Matsuda et al., Structure and physical map of 64 variable segments in the 3'0.8-megabase region of the human immunoglobulin heavy-chain locus. Nat Genet. Jan. 1993;3(1): 88-94.

(56) References Cited

OTHER PUBLICATIONS

Matsuoka et al., Improvement of production rate on recombinant CHO cells in two-stage culture. BMC Proceedings. 2013;7(Suppl 6): P50, 2 pages.
Mazurek et al., The cromolyn binding protein constitutes the Ca2+ channel of basophils opening upon immunological stimulus. Proc Natl Acad Sci U S A. Nov. 1984; 81(21):6841-5.
McKinnon et al., Expression, purification and characterization of secreted recombinant human insulin-like growth factor-I (IGF-I) and the potent variant des(1-3) IGF-I in Chinese hamster ovary cells. J Mol Endocrinol. Jun. 1991;6 (3):231-9.
Mehta et al., Taurine is a weak scavenger of peroxynitrite and does not attenuate sodium nitroprusside toxicity to cells in culture. Amino Acids. 2001;20(4):419-33.
Miao et al., Taurine attenuates lipopolysaccharide-induced disfunction in mouse mammary epithelial cells. Cytokine. Jul. 2012;59(1):35-40.
Michael, Biosynthesis of polyamines and polyamine-containing molecules. Biochem J. Aug. 1, 2016;473(15): 2315-29.
Millipore Sigma, Dulbecco's Modified Eagle Medium (DMEM). Retrieved online at: <https://www.sigmaaldrich.com/US/en/products/cell-culture-and-analysis/cell-culture-media-and-buffers/classical-media-and-buffers/dulbeccos-modified-eagle-medium.> 7 pages, retrieved Oct. 25, 2023.
Milstein et al., Hybrid hybridomas and their use in immunohistochemistry. Nature. Oct. 6-12, 1983;305(5934):537-40.
Moore et al., A modified ninhydrin reagent for the photometric determination of amino acids and related compounds. J Biol Chem. Dec. 1954;211(2):907-13.
Moore et al., Culture of normal human leukocytes. JAMA. Feb. 20, 1967; 199(8): 519-24.
Morimoto et al., Single-step purification of F(ab')2 fragments of mouse monoclonal antibodies (immunoglobulins G1) by hydrophobic interaction high performance liquid chromatography using TSKgel Phenyl-5PW. J Biochem Biophys Methods. Mar. 1992;24(1-2):107-17.
Morrison et al., Cell spreading and the regulation of ornithine decarboxylase. J Cell Sci. Dec. 1995; 108 ( Pt 12):3787-94.
Morrison et al., Chimeric human antibody molecules: mouse antigen-binding domains with human constant region domains. Proc Natl Acad Sci U S A. Nov. 1984;81(21):6851-5.
Morrison, Success in specification. Nature. Apr. 28, 1994;368(6474):812-3.
Mosby's Medical Dictionary, 8th Edition. Elsevier. pp. 1161-1162, (2009).
Mrsny et al., Inhibition of hamster sperm Na+, K+-ATPase activity by taurine and hypotaurine. Life Sci. Jan. 21, 1985;36(3):271-5.
Munson et al., Ligand: a versatile computerized approach for characterization of ligand-binding systems. Anal Biochem. Sep. 1, 1980;107(1):220-39.
Nagae et al., Function and 3D structure of the N-glycans on glycoproteins. Int J Mol Sci. 2012; 13(7): 8398-8429.
Nemkov et al., Three-minute method for amino acid analysis by UHPLC and high-resolution quadrupole orbitrap mass spectrometry. Amino Acids. Nov. 2015;47(11):2345-57.
Neuberger, Generating high-avidity human Mabs in mice. Nat Biotechnol. Jul. 1996; 14(7): 826.
Ni, Progress and Prospect of Antibodies and Antibodies Drug Research. Xiandai Mian Yixue. 2006;26(4):265-268.
Oguchi et al., pH Condition in temperature shift cultivation enhances cell longevity and specific hMab productivity in CHO culture. Cytotechnology. Nov. 2006;52(3): 199-207.
Orlandi et al., Cloning immunoglobulin variable domains for expression by the polymerase chain reaction. Proc Natl Acad Sci U S A. May 1989; 86(10):3833-7.
Orr et al., Survival of animal tissue cells in primary culture in the absence of serum. Appl Microbiol. Jan. 1973;25(1): 49-54.
Orum et al., Efficient method for constructing comprehensive murine Fab antibody libraries displayed on phage. Nucleic Acids Res. Sep. 25, 1993;21(19):4491-8.

Pastorian et al., Tolerance to putrescine toxicity in Chinese hamster ovary cells is associated with altered uptake and export. Exp Cell Res. Mar. 15, 1997;231(2):284-95.
Patkar et al., Flow cytometry as a useful tool for process development: rapid evaluation of expression systems. J Biotechnol. Feb. 28, 2002;93(3):217-29.
Pegg, Regulation of ornithine decarboxylase. J Biol Chem. May 26, 2006;281(21): 14529-32.
Pegg, Toxicity of polyamines and their metabolic products. Chem Res Toxicol. Dec. 16, 2013;26(12): 1782-800.
Petters et al., Addition of Taurine or Hypotaurine to Culture Medium Improves Development of One- and Two-Cell Pig Embryos in Vitro. Theriogenology. Jan. 1991;35(1):253.
Pluckthun et al., Mono- and bivalent antibody fragments produced in Escherichia coli: engineering, folding and antigen binding. Immunol Rev. Dec. 1992; 130:151-88.
Poljak, Production and structure of diabodies. Structure. Dec. 15, 1994;2(12):1121-3.
Presta et al., Humanization of an antibody directed against IgE. J Immunol. Sep. 1, 1993;151(5):2623-32.
Pubchem, Taurine. CID 1123. Retrieved online at: <https://pubchem.ncbi.nlm.nih.gov/compound/Taurine.> 1 page, retrieved Jul. 30, 2020.
Purwaha et al., Targeted metabolomic analysis of amino acid response to L-asparaginase in adherent cells. Metabolomics. 2014;10(5):909-919.
Rasmussen et al., Isolation, characterization and recombinant protein expression in Veggie-CHO: A serum-free CHO host cell line. Cytotechnology. Nov. 1998;28(1-3):31-42.
Reyes et al., Expression of human beta-interferon cDNA under the control of a thymidine kinase promoter from herpes simplex virus. Nature. Jun. 17, 1982;297(5867): 598-601.
Richardson et al., Metabolomics analysis of soy hydrolysates for the identification of productivity markers of mammalian cells for manufacturing therapeutic proteins. Biotechnol Prog. Mar.-Apr. 2015;31(2):522-31.
Riechmann et al., Reshaping human antibodies for therapy. Nature. Mar. 24, 1988;332(6162):323-7.
Ripps et al., Review: taurine: a "very essential" amino acid. Mol Vis. 2012; 18:2673-86.
Ritacco et al., Cell culture media for recombinant protein expression in Chinese hamster ovary (CHO) cells: History, key components, and optimization strategies. Biotechnol Prog. Nov. 2018;34(6): 1407-1426.
Rodrigues et al., Comparison of commercial serum-free media for CHO-K1 cell growth and monoclonal antibody production. Int J Pharm. Nov. 1, 2012;437(1-2):303-5.
Rohrer et al., Profiling N-linked oligosaccharides from IgG by high-performance anion-exchange chromatography with pulsed amperometric detection. Glycobiology. Jun. 2016;26(6):582-91.
Sastry et al., Cloning of the immunological repertoire in Escherichia coli for generation of monoclonal catalytic antibodies: construction of a heavy chain variable region-specific cDNA library. Proc Natl Acad Sci U S A. Aug. 1989; 86(15):5728-32.
Schaffer et al., Clinical significance of taurine. Amino Acids. Jan. 2014;46(1):1-5.
Shalaby et al., Development of humanized bispecific antibodies reactive with cytotoxic lymphocytes and tumor cells overexpressing the HER2 protooncogene. J Exp Med. Jan. 1, 1992;175(1):217-25.
Shantz et al., Regulation of ornithine decarboxylase during oncogenic transformation: mechanisms and therapeutic potential. Amino Acids. Aug. 2007;33(2):213-23.
Shi et al., A high-throughput Automated Platform for the Development of Manufacturing Cell Lines for Protein Therapeutics. J Vis Sci. 2011;55:e3010, 5 pages.
Sidhu et al., Phage-displayed antibody libraries of synthetic heavy chain complementarity determining regions. J Mol Biol. Apr. 23, 2004;338(2):299-310.
Sigma-Aldrich, Ethylenediaminetetraacetic acid tetrasodium salt dihydrate. Retrieved online at: <https://www.sigmaaldrich.com/catalog/product/sigma/e6511?lang=en&region=> 3 pages, retrieved May 26, 2020.

(56) References Cited

OTHER PUBLICATIONS

Sims et al., A humanized CD18 antibody can block function without cell destruction. J Immunol. Aug. 15, 1993;151(4):2296-308.
Singer et al., Genes and Genomes. Moscow, MIR. 1998; 1:63-64.
Skerra, Bacterial expression of immunoglobulin fragments. Curr Opin Immunol. Apr. 1993;5(2):256-62.
Sophie et al., Aflibercept: a Potent Vascular Endothelial Growth Factor Antagonist for Neovascular Age-Related Macular Degeneration and Other Retinal Vascular Diseases. Biol Ther. May 29, 2012;2(1):3, 22 pages.
Stinchcomb et al., Isolation and characterisation of a yeast chromosomal replicator. Nature. Nov. 1, 1979;282(5734):39-43.
Stoner et al., Putrescine stimulates growth of human bronchial epithelial cells in primary culture. In Vitro. May 1980;16(5):399-406.
Suresh et al., Bispecific monoclonal antibodies from hybrid hybridomas. Methods Enzymol. 1986;121:210-28.
Tabuchi et al., Cooverexpression of alanine aminotransferase 1 in Chinese hamster ovary cells overexpressing taurine transporter further stimulates metabolism and enhances product yield. Biotechnol Bioeng. Aug. 2013;110(8):2208-15.
Tabuchi et al., Overexpression of taurine transporter in Chinese hamster ovary cells can enhance cell viability and product yield, while promoting glutamine consumption. Biotechnol Bioeng. Dec. 15, 2010; 107(6):998-1003.
Takeuchi et al., A hyperosmotic stress-induced mRNA of carp cell encodes Na(+)- and Cl(-)-dependent high affinity taurine transporter. Biochim Biophys Acta. Apr. 5, 2000;1464(2):219-30.
Taylor et al., A transgenic mouse that expresses a diversity of human sequence heavy and light chain immunoglobulins. Nucleic Acids Res. Dec. 11, 1992;20(23):6287-95.
The United States Pharmacopeia, The National Formulary. United States Pharmacopeial Convention, Inc., 4 pages, Jan. 1, 2000.
ThermoFisher Scientific, 11320-DMEM/F-12. Technical Resources. Retrieved online at: http://www.thermofisher.com// en/home/technical-resources/media-formulation.55.html. 3 pages, accessed Jan. 19, 2018.
Tobias et al., Exposure to ornithine results in excessive accumulation of putrescine and apoptotic cell death in ornithine decarboxylase overproducing mouse myeloma cells. Cell Growth Differ. Oct. 1995;6(10): 1279-85.
Tome et al., Excess putrescine accumulation inhibits the formation of modified eukaryotic initiation factor 5A (elF-5A) and induces apoptosis. Biochem J. Dec. 15, 1997;328 ( Pt 3)(Pt 3):847-54.
Tomlinson et al., The repertoire of human germline VH sequences reveals about fifty groups of VH segments with different hypervariable loops. J Mol Biol. Oct. 5, 1992;227(3): 776-98.
Toyoda et al., Development of a new protein- and hormone-free medium for hybridoma cultivation. Agric Biol Chem. Jun. 1991;55(6):1631-3.
Traunecker et al., Bispecific single chain molecules (Janusins) target cytotoxic lymphocytes on HIV infected cells. Embo J. Dec. 1991;10(12):3655-9.
Tutt et al., Trispecific F(ab')3 derivatives that use cooperative signaling via the TCR/CD3 complex and CD2 to activate and redirect resting cytotoxic T cells. J Immunol. Jul. 1, 1991;147(1):60-9.
Urlaub et al., Isolation of Chinese hamster cell mutants deficient in dihydrofolate reductase activity. Proc Natl Acad Sci U S A. Jul. 1980;77(7):4216-20.
Van Den Berg et al., Kluyveromyces as a host for heterologous gene expression: expression and secretion of prochymosin. Biotechnology (N Y). Feb. 1990;8(2):135-9.
Verhoeyen et al., Reshaping human antibodies: grafting an antilysozyme activity. Science. Mar. 25, 1988;239(4847):1534-6.
Vijayasankaran et al., Synthesis of poly[(R)-3-hydroxybutyric acid) in the cytoplasm of Pichia pastoris under oxygen limitation. Biomacromolecules. Mar.-Apr. 2005;6(2):604-11.
Vollmers et al., Death by stress: natural IgM-induced apoptosis. Methods Find Exp Clin Pharmacol. Apr. 2005;27(3):185-91.
Vollmers et al., The "early birds": natural IgM antibodies and immune surveillance. Histol Histopathol. Jul. 2005;20(3):927-37.
Wahl et al., Amino acid analysis for pharmacopoeial purposes. Talanta. Jul. 1, 2016;154:150-63.
Wang, New Approved Drugs in the World. pp. 292-295, (2006).
Ward et al., Binding activities of a repertoire of single immunoglobulin variable domains secreted from *Escherichia coli*. Nature. Oct. 12, 1989;341(6242):544-6.
Waterhouse et al., Combinatorial infection and in vivo recombination: a strategy for making large phage antibody repertoires. Nucleic Acids Res. May 11, 1993;21(9):2265-6.
Wikipedia, Ornithine. Retrieved online at: <https://en.wikipedia.org/wiki/Ornithine.> 3 pages, (2020).

\* cited by examiner

CELL CULTURE MEDIUM

CROSS REFERENCE TO RELATED APPLICATION

This application claims the benefit under 35 U.S.C. § 119(e) of U.S. Provisional Application No. 62/925,800, filed Oct. 25, 2019, which is incorporated by reference herein in its entirety.

BACKGROUND

Technical Field

The present disclosure relates to improved cell culture media and manufacturing processes for maintaining and expanding immune effector cells and hematopoietic stem and/or progenitor cells in vitro or ex vivo. More particularly, the disclosure relates to improved media for cell manufacturing that have the characteristics of increasing cell proliferation, viable cell number, therapeutic protein expression, and/or cell potency.

Description of the Related Art

Most cell culture media used for the proliferation and/or maintenance of various cell types (including cell lines and primary cells) are proprietary formulations, the exact composition is not disclosed to the end-user. Commercial cell culture medium manufactures include, but are not limited to, GIBCO, LONZA, INVITROGEN, Millipore Sigma, ThermoFisher Scientific, CellGenix, Fujifilm IrvineScientific, and ATCC.

In recent years, exciting developments in immunotherapy, stem cell biology, and gene editing have fueled the development of novel cell-based therapeutics (e.g., adoptive cellular therapy (ACT) and hematopoietic stem cell transplant (HSCT)). However, cell-based therapeutics have yet to realize their full potential for treating a wide variety of diseases including cancer, infectious disease, autoimmune disease, inflammatory disease, immunodeficiency, and genetic diseases.

As new cell-based treatments are developed, there is an ever increasing need to provide specialized media particularly formulated to achieve the cellular proliferation, maintenance, and phenotypic requirements for each treatment. The importance of cell culture media to regulate and control cellular phenotypes can be seen in the therapeutic antibody space, where there has been extensive research on media to improve protein production and other protein characteristics, such as post-translational modification (e.g., glycosylation profiles). However, the culture media and methods used for protein production are specific for each cell type (e.g., CHO) and are not per se transferable to other cell types (e.g., immune effector cells and/or hematopoietic stem or progenitor cells), let alone primary cell cultures.

Indeed, most, if not all cell-based therapeutic strategies require maintenance of certain cellular phenotypes and/or activation, as well as expansion steps to generate a clinically effective therapeutic dose of cells. Commercially available media may not meet the high standards required for commercialization, let alone regulatory approval. For example, the cells grown in current media may have low viability, slow proliferation, or in the case of T cells, be prone to exhaustion and loss of effector immune cell function when used in large-scale manufacturing. Moreover, improved media which promote increased proliferation, may not only be advantageous for the manufacturer (e.g., reduce resources and costs), it may also improve clinical outcomes by increasing therapeutic potency and reducing the time from bench to bedside.

BRIEF SUMMARY

The present disclosure generally relates, in part, to improved media and related methods of culturing. More particularly, the disclosure relates to improved media and related methods for culturing immune effector cells and/or hematopoietic stem or progenitor cells.

In particular embodiments, a method for culturing, expanding, and/or manufacturing a population of genetically modified immune effector cells or hematopoietic stem or progenitor cells (HSPCs) is provided, comprising culturing the cells in a culture medium comprising L-ornithine, wherein the culture medium has an osmolarity of about 275 mOsm/kg to about 320 mOsm/kg.

In various embodiments, the medium and/or method increases cell proliferation as compared to cells grown in a culture medium without L-ornithine and/or an osmolality of about 275 mOsm/kg to about 320 mOsm/kg.

In various embodiments, the medium and/or method increases cell viability as compared to cells grown in a culture medium without L-ornithine and/or an osmolality of about 275 mOsm/kg to about 320 mOsm/kg.

In various embodiments, the culture medium and/or method increases CD62L+ expression compared to the same or substantially similar cells grown in a culture medium without L-ornithine and/or an osmolality of about 275 mOsm/kg to about 320 mOsm/kg.

In various embodiments, the population of cells are modified to express a therapeutic protein. In some embodiments, the culture medium and/or method increases therapeutic protein expression compared to the same or substantially similar cells grown in a culture medium without L-ornithine and/or an osmolality of about 275 mOsm/kg to about 320 mOsm/kg.

In various embodiments, the cells are cultured at about 36° C. to about 39.5° C. In some embodiments, the cells are cultured at about 36.5° C. to about 39.5° C. In some embodiments, the cells are cultured at about 37° C. to about 39.5° C. In some embodiments, the cells are cultured at about 37.5° C. to about 39.5° C. In some embodiments, the cells are cultured at about 38° C. to about 39.5° C. In some embodiments, the cells are cultured at about 37° C., about 37.5° C., about 38° C., about 38.5° C., about 39° C., or about 39.5° C.

In various embodiments, the culture medium has an osmolarity of about 275 mOsm/kg to about 315 mOsm/kg. In some embodiments, the culture medium has an osmolarity of about 275 mOsm/kg to about 310 mOsm/kg. In some embodiments, the culture medium has an osmolarity of about 275 mOsm/kg to about 305 mOsm/kg. In some embodiments, the culture medium has an osmolarity of about 275 mOsm/kg to about 300 mOsm/kg. In some embodiments, the culture medium has an osmolarity of about 275 mOsm/kg to about 295 mOsm/kg. In some embodiments, the culture medium has an osmolarity of about 275 mOsm/kg to about 290 mOsm/kg. In some embodiments, the culture medium has an osmolarity of about 310 mOsm/kg to about 320 mOsm/kg. In some embodiments, the culture medium has an osmolarity of about 275 mOsm/kg, about 280 mOsm/kg, about 285 mOsm/kg, about 290 mOsm/kg, about 295 mOsm/kg, about 299 mOsm/kg, about 300 mOsm/kg, about 305 mOsm/kg, about 310 mOsm/kg, about 315 mOsm/kg, or about 320 mOsm/kg. In particular embodiments, the medium has an osmolarity of about 310 mOsm/kg.

In various embodiments, the culture medium comprises about 0.75 to about 3.0 mM L-ornithine. In some embodiments, the culture medium comprises about 0.75 to about 3.0 mM L-ornithine. In some embodiments, the culture medium comprises about 0.75 to about 2.5 mM L-ornithine. In some embodiments, the culture medium comprises about 0.75 to about 2.0 mM L-ornithine. In some embodiments, the culture medium comprises about 0.75 to about 1.5 mM L-ornithine. In some embodiments, the culture medium comprises about 1.0 to about 3.0 mM L-ornithine. In some embodiments, the culture medium comprises about 1.5 to about 3.0 mM L-ornithine. In some embodiments, the culture medium comprises about 2.0 to about 3.0 mM L-ornithine. In some embodiments, the culture medium comprises about 2.5 to about 3.0 mM L-ornithine. In particular embodiments, the culture medium comprises about 0.25 g/kg L-ornithine HCL.

In various embodiments, the culture medium comprises a recombinant growth factor. In particular embodiments, the recombinant growth factor increases ornithine decarboxylase (ODC) expression and/or activity. In some embodiments, the recombinant growth factor is a cytokine, optionally an interleukin. In some embodiments, the interleukin is selected from the group consisting of: IL-1, IL-2, IL-3, IL-4, IL-7, IL-10, IL-12, and/or IL-15.

In some embodiments, the interleukin is IL-2, optionally wherein the culture medium comprises about 20 IU/ml to about 500 IU/ml recombinant human IL-2. In some embodiments, the culture medium comprises about 200 IU/ml to about 300 IU/ml recombinant human IL-2. In some embodiments, the culture medium comprises about 250 IU/ml recombinant human IL-2. In some embodiments, the culture medium comprises about 250±25 IU/mL recombinant human IL-2.

In various embodiments, the recombinant growth factor or cytokine is selected from the group consisting of: GM-CSF, G-CSF, IFN-γ, TGFβ, and/or TNFα.

In various embodiments, the culture medium comprises one or more mono- and di-valent salts. In some embodiments, the culture medium comprises NaCl and KCl. In some embodiments, the culture medium comprises a final ratio of NaCl to KCl of about 20:1 to about 30:1. In particular embodiments, the final ratio of NaCl to KCl is about 28:1.

In some embodiments, the culture medium comprises CaCl$_2$), optionally wherein the culture medium comprises about 0.5 mM to about 3 mM CaCl$_2$). In some embodiments, the culture medium comprises 1.89±1.00 mM CaCl$_2$). In some embodiments, the culture medium comprises about 1.89 mM CaCl$_2$).

In various embodiments, the culture medium comprises one or more cell shear protectants. In some embodiments, the one or more cell shear protectants are selected from the group consisting of: polyethylene glycol, polyvinyl alcohol, methylcellulose, simethicone, dextran, serum, albumin, and/or poloxamer. In some embodiments, the culture medium comprises about 0.5 g/kg to about 1.5 g/kg poloxamer 188. In some embodiments, the culture medium comprises about 1 g/kg poloxamer 188. In some embodiments, the culture medium comprises 1±0.1 g/kg poloxamer 188.

In various embodiments, the culture medium comprises an L-alanine-L-glutamine dipeptide, optionally wherein the culture medium comprises about 1 mM to about 3 mM L-alanine-L-glutamine dipeptide. In some embodiments, the culture medium comprises 1 mM to about 3 mM L-alanine-L-glutamine dipeptide. In some embodiments, the culture medium comprises about 1.5 mM to about 3.0 mM L-alanine-L-glutamine dipeptide. In some embodiments, the culture medium comprises about 2 mM to about 3.0 mM L-alanine-L-glutamine dipeptide. In some embodiments, the culture medium comprises 2±0.5 mM L-alanine-L-glutamine dipeptide. In particular embodiments, the culture medium comprises about 2 mM L-alanine-L-glutamine dipeptide.

In various embodiments, the culture medium comprises a buffer. In some embodiments, the buffer is HEPES, optionally wherein the culture medium comprises about 5 mM to about 25 mM HEPES. In some embodiments, the culture medium comprises about 10 mM to about 20 mM HEPES. In some embodiments, the culture medium comprises about 10 mM HEPES.

In various embodiments, the culture medium comprises NaHCO$_3$, optionally wherein the culture medium comprises about 0.40 g/kg to about 0.80 g/kg NaHCO$_3$. In some embodiments, the culture medium comprises about 0.50 g/kg to about 0.7 g/kg NaHCO$_3$. In some embodiments, the culture medium comprises about 0.60 g/kg NaHCO$_3$. In particular embodiments, the culture medium comprises 0.60±0.12 g/kg NaHCO$_3$.

In various embodiments, the culture medium comprises serum or a serum replacement, optionally wherein the culture medium comprises about 40 g/kg to about 60 g/kg heat inactivated (HI) AB serum or gamma irradiated (GI) AB serum. In some embodiments, the culture medium comprises about 45 g/kg to about 55 g/kg HI AB serum or GI AB serum. In some embodiments, the culture medium comprises about 50 g/kg HI human serum or GI AB serum. In particular embodiments, the culture medium comprises 50±2.5 g/kg HI human AB serum or GI AB serum.

In various embodiment, the culture medium comprises a serum and/or human serum albumin (HSA). In some embodiments, the culture medium comprises about 0.5%-5% HSA. In some embodiments, the culture medium comprises about 0.5% HSA, about 1% HSA, about 2% HSA, about 3% HSA, about 4% HSA, or about 5% HSA.

In various embodiments, the culture medium comprises cholesterol. In various embodiments, the culture medium comprises vitamin E.

In various embodiments, the culture medium comprises a base medium for culturing immune cells and/or hematopoietic stem or progenitor cells. In some embodiments, the culture medium comprises about 700 g/kg to about 900 g/kg base medium. In some embodiments, the culture medium comprises about 750 g/kg to about 850 g/kg base medium. In some embodiments, the culture medium comprises about 820 g/kg base medium. In particular embodiments, the culture medium comprises 820±16.5 g/kg base medium.

In further embodiments, the base medium is selected from the group consisting of: X-VIVO™ 15, X-VIVO™ 20, IMDM, RPMI1640, DMEM, DMEM/F12, Ham's, M199, Click's, CTS Optimizer, and AIM V. In particular embodiments, the base medium is X-VIVO™ 15. In particular embodiments the base medium is IMDM or variant thereof.

In particular embodiments, a medium for culturing a population of genetically modified immune effector cells and/or hematopoietic stem or progenitor cells (HSPCs) is provided, comprising:
 a) a base medium for culturing genetically modified immune effector cells or hematopoietic stem or progenitor cells (HSPCs), b) a buffer that maintains the pH of the culture medium in the range of about 6.5 to about 7.5,
c) a serum or serum replacement,
d) one or more mono- and di-valent salts, optionally wherein the mono- and di-valent salts comprise $CaCl_2$), NaCl, and KCl, wherein the final molar ratio of NaCl to KCl in the culture medium is about 20:1 to about 30:1,
e) a recombinant growth factor, or chemically defined replacement, that increases ornithine decarboxylase (ODC) expression and/or activity; and
f) about 0.75 to about 3.0 mM L-ornithine; wherein the cell culture medium has an osmolarity of about 275 mOsm/kg to about 320 mOsm/kg.

In particular embodiments, a medium for culturing a population of genetically modified immune effector cells and/or hematopoietic stem or progenitor cells (HSPCs) is provided, comprising:
a) a base medium comprising X-VIVO™ 15,
b) about 10 mM HEPES buffer,
c) about 50 mL/kg HI Human AB Serum or GI Human AB serum,
d) about 0.60 g/kg $NaHCO_3$,
e) about 1.89 mM $CaCl_2$), about 0.15 g/kg NaCl, and about 0.03 g/kg KCl, wherein the final molar ratio of NaCl to KCl in the culture medium is about 28:1,
f) about 1 g/kg poloxamer 188,
g) about 2 mM L-alanine-L-glutamine dipeptide,
h) about 250 IU/mL recombinant human IL-2 growth factor; and
i) about 0.25 g/kg L-ornithine HCl; wherein the cell culture medium has an osmolarity of about 310 mOsm/kg.

In any of the embodiments described herein, the population of cells can be primary cells. In some embodiments, the population of cells is obtained from peripheral blood mononuclear cells, bone marrow, lymph nodes tissue, cord blood, thymus issue, tissue from a site of infection, ascites, pleural effusion, spleen tissue, or tumors. In some embodiments, the population of immune effector cells comprises cytotoxic T lymphocytes (CTLs), helper T cells, natural killer (NK) cells, or a natural killer T (NKT) cells, regulatory T cells, or dendritic cells. In some embodiments, the population of immune effector cells comprises CD3+, CD4+, and/or CD8+ T cells. In some embodiments, the population of hematopoietic stem or progenitor cells (HSPCs) comprises CD34+ cells. In some embodiments, the population of hematopoietic stem or progenitor cells (HSPCs) comprises CD133+ cells. In some embodiments, the population of hematopoietic stem or progenitor cells (HSPCs) comprises CD44+ cells. In some embodiments, the population of hematopoietic stem or progenitor cells (HSPCs) comprises CD90+ cells.

In any of the embodiments described herein, the population of cells can be derived from a cell-line.

In any embodiment described herein, the population of cells comprises one or more genome edits. In any embodiment described herein, the population of cells are modified to express a therapeutic protein. In some embodiments, the population of cells comprises a gene therapy vector. In some embodiments, the gene therapy vector encodes a therapeutic protein. In some embodiments, the gene therapy vector encodes a chimeric antigen receptor (CAR) or engineered T cell receptor (TCR).

DETAILED DESCRIPTION

A. Overview

Figure 1:
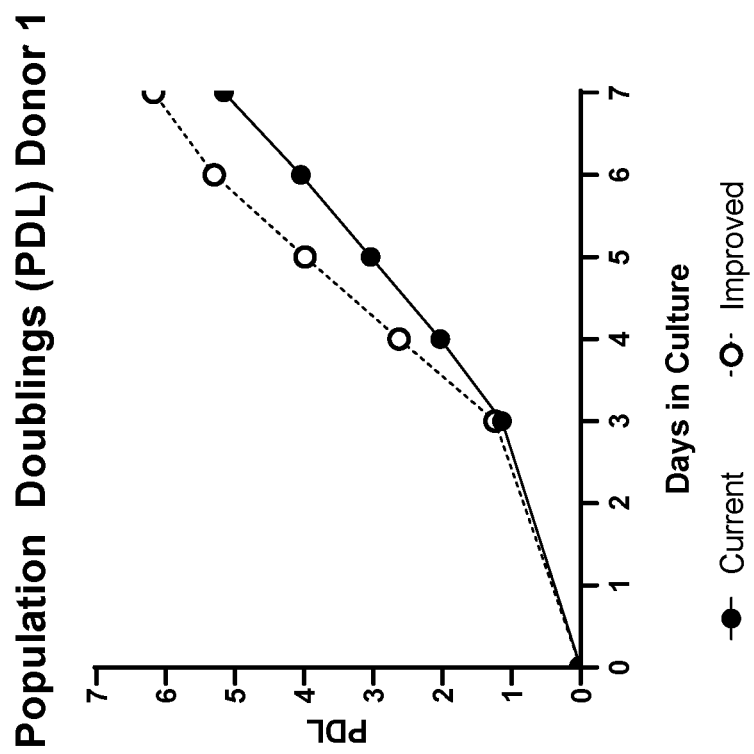
FIG. 1 is a graph showing population doublings (PDL) of CAR-T cells cultured in current and improved medium formulations.

Current commercially available media for culturing immune effector cells or hematopoietic stem or progenitor cells (HSPCs) are proprietary and are not formulated to increase proliferation, while maintaining cell viability and preferred cellular phenotypes.

The present disclosure generally relates to, in part, improved medium formulations for culturing genetically modified immune effector cells or hematopoietic stem or progenitor cells (HSPCs), and related methods. Particularly, the improved formulations disclosed herein surprisingly increase cell proliferation as compared to existing commercially available media, while maintaining cellular phenotypes. Without wishing to be bound by any particular theory, it is contemplated that the improved properties are achieved by reducing osmotic stressors on the cell culturing system while concomitantly facilitating activation of the polyamine synthesis pathway.

In brief, polyamine synthesis is important for maintaining natural function of cells and immune response (Hesterberg et al. *Med. Sci.* (2018) 6(22)). The polyamine synthesis pathway is significant in modulating cell proliferation and maintaining cellular phenotype and/or differentiation. Decreases in polyamine synthesis as a function of age have been recorded in mammalian systems, including clinical observations for humans. This observed decline can shift cellular phenotypes, such as the increase of cell adhesion markers (LFA-1), which may be associated with inflammatory responses (Soda et al., *The Journal of Immunology* (2005) 175:237-245). Furthermore, polyamine deficiencies have been associated with cell death and growth arrest, which were reversed by exogenous polyamine supplementation.

However, administration of polyamine cycle intermediates (e.g., ornithine) were also found to suppress activation of cytotoxic T cells (Droge et al., *The Journal of Immunology* (1985) 134(5):3379-83). Moreover, excess ornithine may also disrupt the TCA/amino acid cycle, disrupt oxidative phosphorylation, increase osmotic stress, and/or activate stress signaling pathways.

The polyamine pathway can also regulate overall osmolarity/tonicity. Osmolarity of human sera is typically between 275-299 mOsm/kg. Higher (and lower) osmotic levels can cause aberrant changes to cell function and volume in which additional energy must be allocated to address. P38 MAPK pathways are utilized by cells in response to environmental stimuli such as osmotic stress (Han et al., *Science* (1994) 365(5173):808-11; Messaoud et al., *PLOS ONE* (2015) 10(9): e0135249), to activate signaling cascades involved in inflammation or inhibit signaling in normal functionality. For example, P38 MAPK can suppress cell cycle progression by modulating PI3K-Akt pathways through shared downstream nodes such as p57 (de Nadal and Posas, *FEBS Journal* (2015) 282:3275-85; Zhao et al., *Cell Cycle* (2013) 12(6):935-43).

Additionally, high osmolarity can inhibit cell proliferation by interfering with energetics required for ion gradient equilibration, along with inhibiting ERK signal transduction pathways. Indeed, polyamine synthesis and osmoregulation are tightly linked in feedback control loops closely regulated by PTEN-PI3K-mTOR and RAS-RAF-MEK-ERK pathways (Casero et al., *Nat Rev Cancer* (2018) 18(11):681-95).

Finally, ornithine decarboxylase (ODC) is an endogenous enzyme that can regulate polyamine synthesis by catalyzing the decarboxylation of ornithine to form putrescine and is the rate limiting step in polyamine synthesis. Accordingly, without wishing to be bound by a particular theory, it is contemplated that tight control of osmolarity and polyamine pathway stimulation (e.g., via ornithine supplementation and/or increased ODC expression) allows for improved cell culture conditions.

Indeed, as disclosed further herein, the inventors have surprisingly discovered improved cell culture media which increase cell proliferation, while maintaining cellular phenotypes over standard cell culture methods/media. Thus, the present invention provides improved methods and media for culturing and/or increasing proliferation of genetically modified immune effector cells (e.g., T cells) or hematopoietic stem or progenitor cells (HSPCs) in vitro or ex vivo.

In various embodiments, a culture medium contemplate herein comprises L-ornithine. In some embodiments, the culture medium comprises about 0.75 mM to about 3.0 mM L-ornithine. In particular embodiments the culture medium comprises about 0.25 g/kg L-ornithine HCl.

In some embodiments, the culture medium comprises a growth factor that increases ODC expression and/or activity, e.g., a cytokine such interleukin 2. In some embodiments the growth factor is a recombinant growth factor. In some embodiments, the growth factor or recombinant growth factor increases ornithine decarboxylase (ODC) expression and/or activity. In some embodiments, the growth factor or recombinant growth factor is a cytokine. In some embodiments, the growth factor or recombinant growth factor is an interleukin.

In various embodiments, the culture medium has an osmolarity of about 275 mOsm/kg to about 320 mOsm/kg. In some embodiments, the culture medium comprises one or more mono- and di-valent salts. In some embodiments, the culture medium comprises NaCl and KCl, wherein the culture medium comprises a final ratio of NaCl to KCl of about 20:1 to about 30:1. In some embodiments, the final ratio of NaCl to KCl is about 28:1. In some embodiments, the culture medium comprises $CaCl_2$). In some embodiments, the culture medium comprises about 0.5 mM to about 3 mM $CaCl_2$).

In various embodiments, the culture medium comprises additional components/additives, including but not limited to, one or more of $NaHCO_3$, serum or a suitable serum replacement (e.g., HI AB serum or GI AB serum), a shear protectant, a reducing agent, and/or a base medium.

In various embodiments, cells suitable for culturing with the disclosed media include, but are not limited to monocytes, immune effector cells, cytotoxic T lymphocytes (CTLs), helper T-cells, natural killer (NK) cells, or natural killer T (NKT) cells, memory T cells (e.g., central memory, effector memory, tissue resident memory or virtual memory T cells), regulatory T cells, dendritic cells, hematopoietic stem or progenitor cells (HSPCs), multipotent progenitor (MPP) cells, common lymphoid progenitor (CLP) cells, early thymic progenitors (ETP) cells and/or cells expressing any number of cellular markers such as CD3+, CD4+, CD8+, CD44+, CD34+, CD90+, and/or CD133+ cells. In some embodiments, the T-cells are CD45RA+, CCR7+, and/or CD25+. In some embodiments, the T-cells do not express, or express relatively low levels of, PD-1, CTLA-4, TIM-3, and/or KLRG1. In some embodiments, the HSPCs are CD90+, CD38− and/or CD45RA−.

In various embodiments, the cells are genetically modified. In some embodiments, the cells comprise one or more genome edits.

In some embodiments, the method comprises culturing the cells at about 37° C. to about 40° C.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid The Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); *Next-Generation Genome Sequencing* (Janitz, 2008 Wiley-VCH); *PCR Protocols (Methods in Molecular Biology)* (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); Handbook Of *Experimental Immunology*, Volumes I-IV (D. M. Weir and C C Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M. Shevach and W. Strober, eds., 1991); *Annual Review of Immunology*; as well as monographs in journals such as *Advances in Immunology*.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below.

The articles "a," "an," and "the" are used herein to refer to one or to more than one (i.e., to at least one, or to one or more) of the grammatical object of the article. By way of example, "an element" means one element or one or more elements.

The use of the alternative (e.g., "of") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, 9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

As used herein, the terms "cell culture," "culture," "culturing," or "cultured" refers to the growth and propagation of cells outside of a multicellular organism or tissue. Suitable culture conditions for mammalian cells are known in the art. See, e.g., Animal cell culture: A Practical Approach, D. Rickwood, ed., Oxford University Press, New York (1992); Animal cell culture methods, Jennie P Mather and David Barnes ed., Academic Press, Massachusetts (1998). Mammalian cells may be cultured in suspension or while attached to a solid substrate. Fluidized bed bioreactors, hollow fiber bioreactors, roller bottles, shake flasks, or stirred tank bioreactors, with or without microcarriers, and operated in a batch, fed batch, continuous, semicontinuous, or perfusion mode are available for mammalian cell culture. Cell culture media or concentrated feed media may be added to the culture continuously or at intervals during the culture. For example, a culture may be fed once per day, every other day, every three days, or may be fed when the concentration of a specific medium component, which is being monitored, falls outside a desired range.

As used herein, the terms "expand," "expanding," "expansion," or "proliferation," refers to symmetrically dividing cells. In particular, it refers to an increase in cell number as compared to the number of cells used to initiate the cell culture.

As used herein, the terms "cell culture media", "media", "cell media", "medium," "cell culture medium" or "culture medium" refers to any nutrient solution used for growing, maintaining, and/or expanding cells, e.g., animal or mammalian cells. Typical, cell culture medium include the following components: a source of energy, which will be usually a carbohydrate compound, preferably glucose, one or more of all essential amino acids, and generally the twenty basic amino acids, plus cysteine, vitamins and/or other organic compounds typically required at low concentrations, lipids or free fatty acids, and inorganic compounds including trace elements, inorganic salts, buffering compounds and nucleosides and bases.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment.

Furthermore, the particular features, structures, or characteristics may be combined in any suitable manner in one or more embodiments. It is also understood that the positive recitation of a feature in one embodiment, serves as a basis for excluding the feature in a particular embodiment.

Additional definitions are set forth throughout this disclosure.

C. Media

Improved media and methods for culturing cells with such media are contemplated herein. In particular embodiments, the media and methods are suitable for culturing, expanding, and/or maintain immune effector cells and/or hematopoietic stem or progenitor cells. The media and methods of culturing contemplated herein provide substantial improvements over current medium formulations for culturing immune effector cells and/or hematopoietic stem or progenitor cells including, but not limited to, increased proliferation and increased viability. In the case of genetically modified immune effector cells, the media and methods of culturing described herein provide improve cellular phenotypes, e.g., increased $CD62L^+$ expression, increased therapeutic protein expression (e.g., $CAR^+$ expression and/or TCR+ expression), while maintaining $CD4^+$ and $CD8^+$ expression. Moreover, in addition to reducing the costs of raw materials for large scale cell manufacturing, the media and methods of culturing contemplated herein reduce the time necessary to expand the cell population, thus reducing the time from bench to bedside.

In particular embodiments, the cell culture media contemplated herein, comprise L-ornithine. As used herein "ornithine" or "L-ornithine" refers to a non-proteinogenic amino acid having the chemical formula $C_5H_{12}N_2O_2$ (CAS Number: 70-26-8). Ornithine is a metabolite of L-arginine which is catalyzed by arginase. In some embodiments, the culture medium comprises about 0.75 mM to about 3.0 mM L-ornithine. In some embodiments, the culture medium comprises about 1 mM to about 3.0 mM L-ornithine. In some embodiments, the culture medium comprises about 1.5 mM to about 3.0 mM L-ornithine. In some embodiments, the culture medium comprises about 2 mM to about 3.0 mM L-ornithine. In some embodiments, the culture medium comprises about 2.5 mM to about 3.0 mM L-ornithine. In some embodiments, the culture medium comprises about 0.75 mM to about 2.5 mM L-ornithine. In some embodiments, the culture medium comprises about 0.75 mM to about 1.5 mM L-ornithine. In some embodiments, the culture medium comprises about 0.75 mM to about 1.0 mM L-ornithine. In some embodiments the culture medium comprises about 0.25 g/kg L-ornithine HCl.

In particular embodiments, the culture medium has an osmolarity of about 275 mOsm/kg to about 330 mOsm/kg. In some embodiments, the culture medium has an osmolarity of about 275 mOsm/kg to about 325 mOsm/kg. In some embodiments, the culture medium has an osmolarity of about 275 mOsm/kg to about 320 mOsm/kg. In some embodiments, the culture medium has an osmolarity of about 275 mOsm/kg to about 315 mOsm/kg. In some embodiments, the culture medium has an osmolarity of about 275 mOsm/kg to about 310 mOsm/kg. In some embodiments, the culture medium has an osmolarity of about 275 mOsm/kg to about 305 mOsm/kg. In some embodiments, the culture medium has an osmolarity of about 275 mOsm/kg to about 300 mOsm/kg. In some embodiments, the culture medium has an osmolarity of about 275 mOsm/kg to about 299 mOsm/kg. In some embodiments, the culture medium has an osmolarity of about 275 mOsm/kg to about 295 mOsm/kg.

In some embodiments, the culture medium has an osmolarity of about 275 mOsm/kg. In some embodiments, the culture medium has an osmolarity of about 280 mOsm/kg. In some embodiments, the culture medium has an osmolarity of about 285 mOsm/kg. In some embodiments, the culture medium has an osmolarity of about 290 mOsm/kg. In some embodiments, the culture medium has an osmolarity of about 299 mOsm/kg. In some embodiments, the culture medium has an osmolarity of about 300 mOsm/kg. In some embodiments, the culture medium has an osmolarity of about 305 mOsm/kg. In some embodiments, the culture medium has an osmolarity of about 310 mOsm/kg. In some embodiments, the culture medium has an osmolarity of about 315 mOsm/kg. In some embodiments, the culture medium has an osmolarity of about 320 mOsm/kg. In some embodiments, the culture medium has an osmolarity of about 325 mOsm/kg. In some embodiments, the culture medium has an osmolarity of about 330 mOsm/kg.

In various embodiments, the culture medium comprises one or more mono- and di-valent salts. In some embodiments, the culture medium comprises NaCl and KCl. Without being bound to a particular theory, it is contemplated that culturing cells in a medium having physiological ratios of NaCl to KCl improves cell proliferation and viability. Accordingly, in some embodiments, the final ratio of NaCl to KCl in the culture media contemplated herein is about 20:1 to about 30:1. In some embodiments, the final ratio of NaCl to KCl is about 21:1 to about 30:1. In some embodiments, the final ratio of NaCl to KCl is about 22:1 to about 30:1. In some embodiments, the final ratio of NaCl to KCl is about 23:1 to about 30:1. In some embodiments, the final ratio of NaCl to KCl is about 24:1 to about 30:1. In some embodiments, the final ratio of NaCl to KCl is about 25:1 to about 30:1. In some embodiments, the final ratio of NaCl to KCl is about 26:1 to about 30:1. In some embodiments, the final ratio of NaCl to KCl is about 27:1 to about 30:1. In some embodiments, the final ratio of NaCl to KCl is about 28:1 to about 30:1.

In some embodiments, the final ratio of NaCl to KCl is about 20:1 to about 29:1. In some embodiments, the final ratio of NaCl to KCl is about 20:1 to about 28:1. In some embodiments, the final ratio of NaCl to KCl is about 20:1 to about 27:1. In some embodiments, the final ratio of NaCl to KCl is about 20:1 to about 26:1. In some embodiments, the final ratio of NaCl to KCl is about 20:1 to about 25:1. In some embodiments, the final ratio of NaCl to KCl is about 20:1 to about 24:1. In some embodiments, the final ratio of NaCl to KCl is about 20:1 to about 23:1. In some embodiments, the final ratio of NaCl to KCl is about 20:1 to about 22:1.

In some embodiments, the final ratio of NaCl to KCl is about 20:1. In some embodiments, the final ratio of NaCl to KCl is about 21:1. In some embodiments, the final ratio of NaCl to KCl is about 22:1. In some embodiments, the final ratio of NaCl to KCl is about 23:1. In some embodiments, the final ratio of NaCl to KCl is about 24:1. In some embodiments, the final ratio of NaCl to KCl is about 25:1. In some embodiments, the final ratio of NaCl to KCl is about 26:1. In some embodiments, the final ratio of NaCl to KCl is about 27:1. In some embodiments, the final ratio of NaCl to KCl is about 28:1. In some embodiments, the final ratio of NaCl to KCl is about 29:1. In some embodiments, the final ratio of NaCl to KCl is about 30:1.

In various embodiments, the culture medium comprises $CaCl_2$). In some embodiments, the culture medium comprises about 0.5 mM to about 3.0 mM $CaCl_2$). In some embodiments, the culture medium comprises about 1.0 mM to about 3.0 mM $CaCl_2$). In some embodiments, the culture medium comprises about 1.5 mM to about 3.0 mM $CaCl_2$). In some embodiments, the culture medium comprises about 2.0 mM to about 3.0 mM $CaCl_2$). In some embodiments, the culture medium comprises about 2.5 mM to about 3.0 mM $CaCl_2$). In some embodiments, the culture medium comprises about 0.5 mM to about 2.5 mM $CaCl_2$). In some embodiments, the culture medium comprises about 0.5 mM to about 2.0 mM $CaCl_2$). In some embodiments, the culture medium comprises about 0.5 mM to about 1.5 mM $CaCl_2$). In some embodiments, the culture medium comprises about 0.5 mM to about 1.0 mM $CaCl_2$).

In various embodiments, the culture medium comprises a growth factor that increases ODC expression and/or activity. As used herein "ornithine decarboxylase," "ODC" or "ODC1" refers to an enzyme (Accession No. NP_001274118) that catalyzes the decarboxylation of ornithine to form putrescine. Without being bound by a particular theory, it is contemplated that increased ODC expression and/or activity, increases the decarboxylation of exogenously added ornithine to the cell culture medium, thus reducing the potential negative side-effects of such addition on the TCA/amino acid cycle, oxidative phosphorylation, and/or osmotic stress.

In some embodiments, the culture medium comprises a recombinant growth factor. In some embodiments, the growth factor or recombinant growth factor increases ornithine decarboxylase (ODC) expression and/or activity. In some embodiments, the growth factor or recombinant growth factor is a cytokine. In some embodiments, the growth factor or recombinant growth factor is an interleukin. In some embodiments, the interleukin is selected from the group consisting of: IL-1, IL-2, IL-3, IL-4, IL-7, IL-10, IL-12, and/or IL-15. In some embodiments, the interleukin is IL-1. In some embodiments, the interleukin is IL-2. In some embodiments, the interleukin is IL-3. In some embodiments, the interleukin is IL-4. In some embodiments, the interleukin is IL-7. In some embodiments, the interleukin is IL-10. In some embodiments, the interleukin is IL-12. In some embodiments, the interleukin is IL-15.

In some embodiments, the culture medium comprises about 20 IU/ml to about 500 IU/ml recombinant interleukin. In some embodiments, the culture medium comprises about 20 IU/ml to about 400 IU/ml recombinant interleukin. In some embodiments, the culture medium comprises about 20 IU/ml to about 300 IU/ml recombinant interleukin. In some embodiments, the culture medium comprises about 20 IU/ml to about 200 IU/ml recombinant interleukin. In some embodiments, the culture medium comprises about 20 IU/ml to about 100 IU/ml recombinant interleukin. In some embodiments, the culture medium comprises about 20 IU/ml to about 95 IU/ml recombinant interleukin. In some embodiments, the culture medium comprises about 20 IU/ml to about 90 IU/ml recombinant interleukin. In some embodiments, the culture medium comprises about 20 IU/ml to about 85 IU/ml recombinant interleukin. In some embodiments, the culture medium comprises about 20 IU/ml to about 80 IU/ml recombinant interleukin. In some embodiments, the culture medium comprises about 20 IU/ml to about 75 IU/ml recombinant interleukin. In some embodiments, the culture medium comprises about 20 IU/ml to about 70 IU/ml recombinant interleukin. In some embodiments, the culture medium comprises about 20 IU/ml to about 65 IU/ml recombinant interleukin. In some embodiments, the culture medium comprises about 20 IU/ml to about 60 IU/ml recombinant interleukin. In some embodiments, the culture medium comprises about 20 IU/ml to about 55 IU/ml recombinant interleukin. In some embodiments, the culture medium comprises about 20 IU/ml to about 50 IU/ml recombinant interleukin. In some embodiments, the culture medium comprises about 20 IU/ml to about 45 IU/ml recombinant interleukin. In some embodiments, the culture medium comprises about 20 IU/ml to about 40 IU/ml recombinant interleukin. In some embodiments, the culture medium comprises about 20 IU/ml to about 35 IU/ml recombinant interleukin. In some embodiments, the culture medium comprises about 20 IU/ml to about 30 IU/ml recombinant interleukin. In some embodiments, the culture medium comprises about 20 IU/ml to about 25 IU/ml recombinant interleukin. In some embodiments, the culture medium comprises about 20 IU/ml, about 25 IU/ml, about 30 IU/ml, about 35 IU/ml, about IU/ml, about 45 IU/ml, about 50 IU/ml, about 55 IU/ml, about 60 IU/ml, about 65 IU/ml, about 70 IU/ml, about 75 IU/ml, about 80 IU/ml, about 85 IU/ml, about 90 IU/ml, about 95 IU/ml, about 100 IU/ml, about 150 IU/ml, about 200 IU/ml, about 250 IU/ml, about 300 IU/ml, about 350 IU/ml, about 400 IU/ml, about 450 IU/ml, or about 500 IU/ml, recombinant interleukin.

In some embodiments, the culture medium comprises about 200 IU/ml to about 300 IU/ml recombinant interleukin. In some embodiments, the culture medium comprises about 200 IU/ml to about 300 IU/ml recombinant interleukin. In some embodiments, the culture medium comprises about 200 IU/ml recombinant interleukin. In some embodiments, the culture medium comprises about 210 IU/ml recombinant interleukin. In some embodiments, the culture medium comprises about 220 IU/ml recombinant interleukin. In some embodiments, the culture medium comprises about 230 IU/ml recombinant interleukin. In some embodiments, the culture medium comprises about 240 IU/ml recombinant interleukin. In some embodiments, the culture medium comprises about 250 IU/ml recombinant interleukin. In some embodiments, the culture medium comprises about 260 IU/ml recombinant interleukin. In some embodiments, the culture medium comprises about 270 IU/ml recombinant interleukin. In some embodiments, the culture medium comprises about 280 IU/ml recombinant interleukin. In some embodiments, the culture medium comprises about 290 IU/ml recombinant interleukin. In some embodiments, the culture medium comprises about 300 IU/ml recombinant interleukin. In some embodiments, the recombinant growth factors are of human origin. In some embodiments, the culture medium comprises about 250±25 IU/mL recombinant human IL-2.

In some embodiments, the growth factor, cytokine, or recombinant version thereof is selected from the group consisting of: GM-CSF, G-CSF, IFN-γ, TGFβ, and/or TNFα. In some embodiments, the culture media comprises recombinant GM-CSF. In some embodiments, the culture media comprises recombinant G-CSF. In some embodiments, the culture media comprises recombinant IFN-7. In some embodiments, the culture media comprises recombinant TGFβ. In some embodiments, the culture media comprises recombinant TNFα.

In various embodiments, the culture medium comprises $NaHCO_3$. In some embodiments, the culture medium comprises about 0.40 g/kg to about 0.80 g/kg $NaHCO_3$.

In some embodiments, the culture medium comprises about 0.50 g/kg to about 0.80 g/kg $NaHCO_3$. In some embodiments, the culture medium comprises about 0.60 g/kg to about 0.80 g/kg $NaHCO_3$. In some embodiments, the culture medium comprises about 0.70 g/kg to about 0.80 g/kg $NaHCO_3$. In some embodiments, the culture medium comprises about 0.40 g/kg to about 0.70 g/kg NaHCO$_3$. In some embodiments, the culture medium comprises about 0.40 g/kg to about 0.60 g/kg NaHCO$_3$. In some embodiments, the culture medium comprises about 0.40 g/kg to about 0.50 g/kg NaHCO$_3$. In some embodiments, the culture medium comprises about 0.40 g/kg NaHCO$_3$. In some embodiments, the culture medium comprises about 0.50 g/kg NaHCO$_3$. In some embodiments, the culture medium comprises about 0.60 g/kg NaHCO$_3$. In some embodiments, the culture medium comprises about 0.70 g/kg NaHCO$_3$. In some embodiments, the culture medium comprises about 0.80 g/kg NaHCO$_3$. In some embodiments, the culture medium comprises 0.60±0.12 g/kg NaHCO$_3$.

In various embodiments, the culture medium comprises serum or a serum replacement. As used herein "serum replacement" or "serum replacement media" refers to a composition that can be used in conjunction with a basal media or as a complete media in order to promote cell growth and survival in culture. In various embodiments, serum replacement is used in basal or complete media as a replacement for any serum that is characteristically added to media for culture of cells in vitro. It is contemplated that the serum replacement comprises proteins and other factors for growth and survival of cells in culture. In various embodiments, the serum replacement is added to a basal media prior to use in cell culture. It is further contemplated that, in various embodiments, a serum replacement may comprise a base media and base nutrients such as salts, amino acids, vitamins, trace elements, antioxidants, and the like, such that the serum replacement is useful as a serum-free complete media for cell culture.

In some embodiments, the serum is a human serum. In some embodiments, the serum is "heat inactivated" (HI). In some embodiments, the serum is "gamma irradiated" (GI). In some embodiments the serum is human AB serum. As used herein "serum AB" or "AB serum" refers to human serum from type AB donors which lack antibodies against the A and B blood-type antigens.

In some embodiments, the culture medium comprises about 6% v/v serum or serum replacement. In some embodiments, the culture medium comprises about 5% v/v serum or serum replacement. In some embodiments, the culture medium comprises about 4% v/v serum or serum replacement. In some embodiments, the culture medium comprises about 3% v/v serum or serum replacement. In some embodiments, the culture medium comprises about 2% v/v serum or serum replacement. In some embodiments, the culture medium comprises about 1% v/v serum or serum replacement. In some embodiments, the culture medium comprises about 0.5% v/v serum or serum replacement. In certain embodiments, the culture medium is serum-free, i.e., the medium does not comprise any serum or serum replacement.

In particular embodiments, the culture medium comprises about 40 g/kg to about 60 g/kg heat inactivated (HI) AB serum or gamma irradiated (GI) AB serum. In some embodiments, the culture medium comprises about 40 g/kg to about 60 g/kg heat inactivated (HI) AB serum or gamma irradiated (GI) AB serum. In some embodiments, the culture medium comprises about 45 g/kg to about 60 g/kg heat inactivated (HI) AB serum or gamma irradiated (GI) AB serum. In some embodiments, the culture medium comprises about 50 g/kg to about 60 g/kg heat inactivated (HI) AB serum or gamma irradiated (GI) AB serum. In some embodiments, the culture medium comprises about 55 g/kg to about 60 g/kg heat inactivated (HI) AB serum or gamma irradiated (GI) AB serum. In some embodiments, the culture medium comprises about 40 g/kg to about 55 g/kg heat inactivated (HI) AB serum or gamma irradiated (GI) AB serum. In some embodiments, the culture medium comprises about 40 g/kg to about 50 g/kg heat inactivated (HI) AB serum or gamma irradiated (GI) AB serum. In some embodiments, the culture medium comprises about 40 g/kg to about 45 g/kg heat inactivated (HI) AB serum or gamma irradiated (GI) AB serum. In some embodiments, the culture medium comprises about 40 g/kg heat inactivated (HI) AB serum or gamma irradiated (GI) AB serum. In some embodiments, the culture medium comprises about 45 g/kg heat inactivated (HI) AB serum or gamma irradiated (GI) AB serum. In some embodiments, the culture medium comprises about 50 g/kg heat inactivated (HI) AB serum or gamma irradiated (GI) AB serum. In some embodiments, the culture medium comprises about 55 g/kg heat inactivated (HI) AB serum or gamma irradiated (GI) AB serum. In some embodiments, the culture medium comprises about 60 g/kg heat inactivated (HI) AB serum or gamma irradiated (GI) AB serum. In some embodiments, the culture medium comprises 50±2.5 g/kg heat inactivated (HI) human AB serum or gamma irradiated (GI) AB serum.

In various embodiment, the culture medium comprises a serum and/or human serum albumin (HSA).

In some embodiments, the culture medium comprises about 0.5% HSA. In some embodiments, the culture medium comprises about 1% HSA. In some embodiments, the culture medium comprises about 2% HSA. In some embodiments, the culture medium comprises about 3% HSA. In some embodiments, the culture medium comprises about 4% HSA. In some embodiments, the culture medium comprises about 5% HSA. In some embodiments, the culture medium comprises about 0.5% to about 5% HSA. In some embodiments, the culture medium comprises about 1% to about 5% HSA. In some embodiments, the culture medium comprises about 1% to about 3% HSA. In some embodiments, the culture medium comprises about 2% to about 4% HSA.

In various embodiments, the culture medium comprises cholesterol. In various embodiments, the culture medium comprises vitamin E.

In various embodiments, the culture medium comprises a base medium suitable for culturing immune cells and/or hematopoietic stem or progenitor cells. As used herein, the term "base Medium" or "basal medium" refers to a medium useful for mammalian cell culture comprising a carbon source such as a sugar, lipids, vitamins and amino acids and a buffering system to maintain the medium within the physiological pH range. The medium contains levels and/or ratios of salts and nutrients needed to support immune effector cell and/or hematopoietic stem or progenitor cell expansion and vitality. The medium may be in dry or liquid form, and may be prepared from a plurality of separate stock compositions (e.g., each independently existing in dry or solution form) that can be combined prior to use. For example, the medium may be prepared from two, three, four, or more stock compositions (each independently in dry or solution form), and where necessary mixed with aqueous diluent prior to use to give a 1× medium formulation. For example, standard 1× base media may include, but are not limited to, MSCGM-CD, X-VIVO™ medium (e.g., X-VIVO™15 or X-VIVO™20), EAGLE, Basal Medium Eagle (BME), Iscove's Modified Dulbecco's medium (IMDM), or a variation thereof, RPMI1640, Dulbecco's Modified Eagle's Medium (DMEM), Minimal Essential Medium (MEM), α-Minimal Essential Medium "αMEM", Glasgow's Minimal Essential Medium (G-MEM), DMEM/F12, Ham's, M199, Click's, CTS™ Optimizer™ and AIM V. A base media can be supplemented with nutrients as described herein. In particular embodiments, the selection of suitable base media is within the ambit of ordinary skill in the art of cell culture.

In particular embodiments, the base medium is selected from the group consisting of: X-VIVO™ 15, X-VIVO™ 20, IMDM, RPMI1640, DMEM, DMEM/F12, Ham's, M199, Click's, CTS™ Optimizer™, and AIM V. In some embodiments, the base medium is X-VIVO™ 15. In some embodiments, the base medium is X-VIVO™ 20. In some embodiments, the base medium is MDM or a variation thereof. In some embodiments, the base medium is RPMI1640 or a variation thereof. In some embodiments, the base medium is DMEM or a variation thereof. In some embodiments, the base medium is DMEM/F12 or a variation thereof. In some embodiments, the base medium is Ham's or a variation thereof. In some embodiments, the base medium is M199 or a variation thereof. In some embodiments, the base medium is Click's or a variation thereof. In some embodiments, the base medium is CTS™ Optimizer™ or a variation thereof. In some embodiments, the base medium is AIM V or a variation thereof.

In some embodiments, the culture medium comprises about 700 g/kg to about 900 g/kg base medium. In some embodiments, the culture medium comprises about 750 g/kg to about 900 g/kg base medium. In some embodiments, the culture medium comprises about 800 g/kg to about 900 g/kg base medium. In some embodiments, the culture medium comprises about 850 g/kg to about 900 g/kg base medium. In some embodiments, the culture medium comprises about 700 g/kg to about 850 g/kg base medium. In some embodiments, the culture medium comprises about 700 g/kg to about 800 g/kg base medium. In some embodiments, the culture medium comprises about 700 g/kg to about 750 g/kg base medium. In some embodiments, the culture medium comprises about 700 g/kg base medium. In some embodiments, the culture medium comprises about 750 g/kg base medium. In some embodiments, the culture medium comprises about 800 g/kg base medium. In some embodiments, the culture medium comprises about 850 g/kg base medium. In some embodiments, the culture medium comprises about 900 g/kg base medium. In some embodiments, the culture medium comprises about 820 g/kg base medium. In some embodiments, the culture medium comprises 820±16.5 g/kg base medium.

In various embodiments, the culture medium comprises one or more shear protectants. As used herein, a "shear protectant" refers to a defined compound or reagent which may be added to a cell culture medium to provide a level of protection against shearing forces which may be prevalent in cell manufacturing vessels, e.g., dishes, flasks, bags, and/or bioreactors. A "shear protectant", includes, but is not limited to, compounds such as hydroxyethyl starch, derivatives of cellulose, serum, tryptosephosphate, polyvinyl alcohol (PVA), bovine serum albumin, polyethylene glycol (PEG), poloxamers, methylcellulose, simethicone, and/or dextran, as well as any combination thereof. These compounds offer protection from shear related cell damage for various mechanisms, but do not promote lysis of the cells, such as detergents like Triton X. In particular embodiments, the selection of suitable shear protectants is within the ambit of ordinary skill in the art of cell culture.

In some embodiments, the shear protectant is selected from the group consisting of: polyethylene glycol, polyvinyl alcohol, methylcellulose, simethicone, dextran, serum, albumin, and poloxamer. In some embodiments, the culture medium comprises a polyethylene glycol. In some embodiments, the culture medium comprises a polyvinyl alcohol. In some embodiments, the culture medium comprises a methylcellulose. In some embodiments, the culture medium comprises a simethicone. In some embodiments, the culture medium comprises a dextran. In some embodiments, the culture medium comprises a serum. In some embodiments, the culture medium comprises an albumin.

In some embodiments, the culture medium comprises a poloxamer. In some embodiments, the culture medium comprises about 0.5 g/kg to about 1.5 g/kg poloxamer. In some embodiments, the culture medium comprises about 0.6 g/kg to about 1.5 g/kg poloxamer. In some embodiments, the culture medium comprises about 0.7 g/kg to about 1.5 g/kg poloxamer. In some embodiments, the culture medium comprises about 0.8 g/kg to about 1.5 g/kg poloxamer. In some embodiments, the culture medium comprises about 0.9 g/kg to about 1.5 g/kg poloxamer. In some embodiments, the culture medium comprises about 1.0 g/kg to about 1.5 g/kg poloxamer. In some embodiments, the culture medium comprises about 1.1 g/kg to about 1.5 g/kg poloxamer. In some embodiments, the culture medium comprises about 1.2 g/kg to about 1.5 g/kg poloxamer. In some embodiments, the culture medium comprises about 1.3 g/kg to about 1.5 g/kg poloxamer. In some embodiments, the culture medium comprises about 1.4 g/kg to about 1.5 g/kg poloxamer. In some embodiments, the culture medium comprises about 0.5 g/kg to about 1.4 g/kg poloxamer. In some embodiments, the culture medium comprises about 0.5 g/kg to about 1.3 g/kg poloxamer. In some embodiments, the culture medium comprises about 0.5 g/kg to about 1.2 g/kg poloxamer. In some embodiments, the culture medium comprises about 0.5 g/kg to about 1.1 g/kg poloxamer. In some embodiments, the culture medium comprises about 0.5 g/kg to about 1.0 g/kg poloxamer. In some embodiments, the culture medium comprises about 0.5 g/kg to about 0.9 g/kg poloxamer. In some embodiments, the culture medium comprises about 0.5 g/kg to about 0.8 g/kg poloxamer. In some embodiments, the culture medium comprises about 0.5 g/kg to about 0.7 g/kg poloxamer. In some embodiments, the culture medium comprises about 0.5 g/kg to about 0.6 g/kg poloxamer. In some embodiments, the culture medium comprises about 0.5 g/kg poloxamer. In some embodiments, the culture medium comprises about 0.6 g/kg poloxamer. In some embodiments, the culture medium comprises about 0.7 g/kg poloxamer. In some embodiments, the culture medium comprises about 0.8 g/kg poloxamer. In some embodiments, the culture medium comprises about 0.9 g/kg poloxamer. In some embodiments, the culture medium comprises about 1.0 g/kg poloxamer. In some embodiments, the culture medium comprises about 1.1 g/kg poloxamer. In some embodiments, the culture medium comprises about 1.2 g/kg poloxamer. In some embodiments, the culture medium comprises about 1.3 g/kg poloxamer. In some embodiments, the culture medium comprises about 1.4 g/kg poloxamer. In some embodiments, the culture medium comprises about 1.5 g/kg poloxamer.

In some embodiments, the culture medium comprises poloxamer 181. In some embodiments, the culture medium comprises poloxamer 188. In particular embodiments, the culture medium comprises about 1.0 g/kg poloxamer 188. In particular embodiments, the culture medium comprises 1±0.1 g/kg poloxamer 188.

In various embodiments, the culture medium comprises an L-alanine-L-glutamine dipeptide. In some embodiments, the culture medium comprises about 1 mM to about 3 mM L-alanine-L-glutamine dipeptide. In some embodiments, the culture medium comprises about 1.5 mM to about 3 mM L-alanine-L-glutamine dipeptide. In some embodiments, the culture medium comprises about 2 mM to about 3 mM L-alanine-L-glutamine dipeptide. In some embodiments, the culture medium comprises about 2.5 mM to about 3 mM L-alanine-L-glutamine dipeptide. In some embodiments, the culture medium comprises about 1 mM to about 2.5 mM L-alanine-L-glutamine dipeptide. In some embodiments, the culture medium comprises about 1 mM to about 2 mM L-alanine-L-glutamine dipeptide. In some embodiments, the culture medium comprises about 1 mM to about 1.5 mM L-alanine-L-glutamine dipeptide. In some embodiments, the culture medium comprises about 1 mM to about 3 mM L-alanine-L-glutamine dipeptide. In some embodiments, the culture medium comprises about 1 mM L-alanine-L-glutamine dipeptide. In some embodiments, the culture medium comprises about 1.5 mM L-alanine-L-glutamine dipeptide. In some embodiments, the culture medium comprises about 2 mM L-alanine-L-glutamine dipeptide. In some embodiments, the culture medium comprises about 2.5 mM L-alanine-L-glutamine dipeptide. In some embodiments, the culture medium comprises about 3 mM L-alanine-L-glutamine dipeptide. In particular embodiments, the culture medium comprises 2±0.5 mM L-alanine-L-glutamine dipeptide.

In various embodiments, the culture medium can optionally include one or more buffering agents (e.g., a buffer). A buffering agent suitable for use in particular embodiments contemplated herein includes one that provides buffering capacity without substantial cytotoxicity to the cells cultured, and maintains the pH of the culture medium in the range of about 6.5 to about 7.5 during culture. In some embodiments, the buffer maintains the pH of the culture medium in the range of about 6.8 to about 7.2 throughout the culture. Illustrative examples of buffering agents suitable for use in particular embodiments contemplated herein include, but are not limited to, carbonates (e.g. $NaHCO_3$), chlorides (e.g. $CaCl_2$), sulphates (e.g. $MgSO_4$) and phosphates (e.g. $NaH_2PO_4$). These buffers are generally used at about 50 to about 500 mg/l. Other buffers such as N-[2-hydroxyethyl]-piperazine-N'-[2-ethanesul-phonic acid] (HEPES), 2-(N-morpholino)ethanesulfonic acid (MES), and 3-[N-morpholinoj-propanesulfonic acid (MOPS) may also be used in particular embodiments.

In particular embodiments, the culture medium comprises a HEPES buffer. In some embodiments, the culture medium comprises about 5 mM to about 25 mM HEPES. In some embodiments, the culture medium comprises about 10 mM to about 25 mM HEPES. In some embodiments, the culture medium comprises about 15 mM to about 25 mM HEPES. In some embodiments, the culture medium comprises about 20 mM to about 25 mM HEPES. In some embodiments, the culture medium comprises about 5 mM to about 20 mM HEPES. In some embodiments, the culture medium comprises about 5 mM to about 15 mM HEPES. In some embodiments, the culture medium comprises about 5 mM to about 10 mM HEPES. In some embodiments, the culture medium comprises about 5 mM HEPES. In some embodiments, the culture medium comprises about 10 mM HEPES. In some embodiments, the culture medium comprises about 15 mM HEPES. In some embodiments, the culture medium comprises about 20 mM HEPES. In some embodiments, the culture medium comprises about 25 mM HEPES.

In various embodiments, the culture medium further comprises one or more reducing agents. In some embodiments, the reducing agent is dithiothreitol (DTT). In some embodiments, the reducing agent is glutathione or reduced glutathione (rGSH). In some embodiments, the reducing agent is L-cysteine (Cys). In some embodiments, the reducing agent is Coenzyme A, lipoic acid, thioredoxin, or glutaredoxin. In some embodiments, the reducing agent is beta mercaptoethanol (2-mercaptoethanol).

In particular embodiments, the culture medium comprises about 10 µM to about 500 µM 2-mercaptoethanol. In some embodiments, the culture medium comprises about 10 µM to about 400 µM 2-mercaptoethanol. In some embodiments, the culture medium comprises about 10 µM to about 300 µM 2-mercaptoethanol. In some embodiments, the culture medium comprises about 10 µM to about 200 µM 2-mercaptoethanol. In some embodiments, the culture medium comprises about 10 µM to about 100 µM 2-mercaptoethanol. In some embodiments, the culture medium comprises about 10 µM to about 90 µM 2-mercaptoethanol. In some embodiments, the culture medium comprises about 10 µM to about 80 µM 2-mercaptoethanol. In some embodiments, the culture medium comprises about 10 µM to about 70 µM 2-mercaptoethanol. In some embodiments, the culture medium comprises about 10 µM to about 60 µM 2-mercaptoethanol. In some embodiments, the culture medium comprises about 10 µM to about 50 µM 2-mercaptoethanol. In some embodiments, the culture medium comprises about 10 µM to about 40 µM 2-mercaptoethanol. In some embodiments, the culture medium comprises about 10 µM to about 30 µM 2-mercaptoethanol. In some embodiments, the culture medium comprises about 10 µM to about 20 µM 2-mercaptoethanol. In some embodiments, the culture medium comprises about 10 µM 2-mercaptoethanol. In some embodiments, the culture medium comprises about 15 µM 2-mercaptoethanol. In some embodiments, the culture medium comprises about 20 µM 2-mercaptoethanol. In some embodiments, the culture medium comprises about 25 µM 2-mercaptoethanol. In some embodiments, the culture medium comprises about 30 µM 2-mercaptoethanol. In some embodiments, the culture medium comprises about 35 µM 2-mercaptoethanol. In some embodiments, the culture medium comprises about 40 µM 2-mercaptoethanol. In some embodiments, the culture medium comprises about 45 µM 2-mercaptoethanol. In some embodiments, the culture medium comprises about 50 µM 2-mercaptoethanol. In some embodiments, the culture medium comprises about 55 µM 2-mercaptoethanol. In some embodiments, the culture medium comprises about 60 µM 2-mercaptoethanol. In some embodiments, the culture medium comprises about 70 µM 2-mercaptoethanol. In some embodiments, the culture medium comprises about 80 µM 2-mercaptoethanol. In some embodiments, the culture medium comprises about 90 µM 2-mercaptoethanol. In some embodiments, the culture medium comprises about 100 µM 2-mercaptoethanol.

In various embodiments, the pH of the media disclosed herein are adjusted to values that allow the growth of the cells, e.g. at values between about pH 6.5 and about pH 7.5. In some embodiments, the media disclosed herein are adjusted to a pH between about 6.8 and about 7.2. In some embodiments, the culture medium has a pH of about 6.8. In some embodiments, the culture medium has a pH of about 6.9. In some embodiments, the culture medium has a pH of about 7.0. In some embodiments, the culture medium has a pH of about 7.1. In some embodiments, the culture medium has a pH of about 7.2.

In various embodiments, the temperature of the cell culture is selected in a range where cells are viable and grow. A typical temperature for cell culturing is in the range between about 36.5° C. and about 37.5° C. However, the exact temperature can be adapted to the needs of the cells and also changed during culturing to allow their optimal viability, growth or production. Moreover, without being bound by a particular theory, it is contemplated herein, that higher temperatures (e.g., those that could mimic a fever) may increase proliferation of the cells.

Accordingly, in various embodiments, the cells are cultured at about 36° C. to about 39.5° C. In some embodiments, the cells are cultured at about 36.5° C. to about 39.5° C. In some embodiments, the cells are cultured at about 37° C. to about 39.5° C. In some embodiments, the cells are cultured at about 37.5° C. to about 39.5° C. In some embodiments, cells are cultured at about 38° C. to about 39.5° C. In some embodiments, the cells are cultured at about 37° C., about 37.5° C., about 38° C., about 38.5° C., about 39° C., or about 39.5° C. In particular embodiments, the cells are cultured at about 38° C. In other embodiments, the cells are cultured at about 39° C.

In various embodiments, cells suitable for culturing with the disclosed media include, but are not limited to monocytes, immune effector cells, cytotoxic T lymphocytes (CTLs), helper T-cells, natural killer (NK) cells, or natural killer T (NKT) cells, memory T cells, regulatory T cells, dendritic cells, hematopoietic stem or progenitor cells (HSPCs), multipotent progenitor (MPP) cells, common lymphoid progenitor (CLP) cells, early thymic progenitors (ETP) cells and/or cells expressing any number of cellular markers such as CD3+, CD4+, CD8+, CD44+, CD34+, and CD133+ cells. In some embodiments, the T-cells are CD45RA+, CCR7+, and/or CD25+. In some embodiments, the T-cells do not express, or express relatively low levels of, PD-1, CTLA-4, TIM-3, and/or KLRG1. In some embodiments, the HSPCs are CD90+, CD38– and/or CD45RA–.

In some embodiments, the cells are genetically modified.

The immune effector cells and/or hematopoietic stem cells used to inoculate the cell culture may be derived from any source including bone marrow, both adult and fetal cytokine or chemotherapy mobilized peripheral blood, fetal liver, bone marrow or umbilical cord blood.

Any suitable expansion container, vessel, flask, or appropriate tube such as a 24 well plate, 12.5 cm$^2$ T flask or gas permeable bag can be used in the methods of the present disclosure. Such culture containers are commercially available, for example, from Falcon Corning or Costor. In preferred embodiments, the cells are manufactured/cultured under good manufacturing practice (GMP).

D. Cells and Cell Therapies

The media and methods contemplated herein are suitable for culturing various cell types, e.g., immune effector cells and/or hematopoietic stem or progenitor cells. In particular embodiments, the media and methods are useful for culturing cells for cell-based therapies, including but not limited to adoptive cell therapies, genome edited cell therapies, and cell-based gene therapies. In preferred embodiments, the media and methods are useful for increasing cell proliferation as compared to similar unoptimized media. For example, in particular embodiments, a method for increasing proliferation of, culturing, and/or expanding a population of immune effector cells and/or hematopoietic stem or progenitor cells (HSPCs) is provided. In preferred embodiments, the method comprises culturing the cells in a medium comprising L-ornithine, wherein the culture medium has an osmolarity of about 275 mOsm/kg to about 320 mOsm/kg, and wherein the proliferation is increased as compared to the same or substantially similar cells grown in medium without L-ornithine and/or an osmolality of about 275 mOsm/kg to about 320 mOsm/kg.

In particular embodiments, the media and methods described herein are useful for increasing proliferation of, culturing, manufacturing, and/or expanding a cell-based therapy comprising genetically modified cells. In particular embodiments, the genetically modified cells comprise one or more vectors encoding a therapeutic transgene, e.g., a globin, an engineered antigen receptor. Illustrative examples of vectors include, but are not limited to, viral vectors. Illustrative examples of viral vectors include, but are not limited to: an adenovirus, an adeno-associated virus (AAV), a retrovirus, e.g., a lentivirus (e.g., HIV-1, HIV-2), a herpes simplex virus e.g., HSV-1, HSV-2), or a vaccinia virus. In particular embodiments, the genetically modified cells comprise one or more genome edits. In certain embodiments, the genetically modified cells comprise one or more vectors comprising a polynucleotide encoding a therapeutic transgene and one or more gene edits.

In particular embodiments, the media and methods contemplated herein are used to increasing proliferation of, culturing, manufacturing, and/or expanding cell-therapies for the prevention, treatment, or amelioration of at least one symptom, of a monogenetic disease, disorder, or condition, e.g., a hemoglobinopathy, cerebral adrenoleukodystrophy, cancer, GVHD, infectious disease, autoimmune disease, immunodeficiency or condition associated therewith.

Cells suitable for culturing, manufacturing, and/or expanding in the media and methods contemplated herein particular embodiments may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject. In an even more preferred embodiment, the cells are obtained from a human subject. In another preferred embodiment, the cells are obtained from a human subject that will be treated with the cell-based therapy.

An "isolated cell" refers to a non-naturally occurring cell, e.g., a cell that does not exist in nature, a modified cell, an engineered cell, etc., that has been obtained from an in vivo tissue or organ and is substantially free of extracellular matrix.

As used herein, the term "population of cells" refers to a plurality of cells that may be made up of any number and/or combination of homogenous or heterogeneous cell types, as described elsewhere herein. For example, a population of cells may comprise about 10%, about 20%, about 30%, about 40%, about 50%, about 60%, about 70%, about 80%, about 90%, or about 100% of a desired therapeutic cell type, e.g., hematopoietic stem or progenitor cells, immune effector cells. In certain embodiments, the cultured cells are isolated or purified from a population of heterogeneous cells using methods known in the art.

Illustrative examples of cell types for increasing proliferation, culturing, manufacturing, and/or expanding in the media and methods contemplated herein include, but are not limited to, cell lines, primary cells, stem cells, progenitor cells, and differentiated cells.

The term "stem cell" refers to a cell which is an undifferentiated cell capable of (1) long term self-renewal, or the ability to generate at least one identical copy of the original cell, (2) differentiation at the single cell level into multiple, and in some instance only one, specialized cell type and (3)

of in vivo functional regeneration of tissues. Stem cells are subclassified according to their developmental potential as totipotent, pluripotent, multipotent and oligo/unipotent. "Self-renewal" refers a cell with a unique capacity to produce unaltered daughter cells and to generate specialized cell types (potency). Self-renewal can be achieved in two ways. Asymmetric cell division produces one daughter cell that is identical to the parental cell and one daughter cell that is different from the parental cell and is a progenitor or differentiated cell. Symmetric cell division produces two identical daughter cells. "Proliferation" or "expansion" of cells refers to symmetrically dividing cells.

As used herein, the term "progenitor" or "progenitor cells" refers to cells have the capacity to self-renew and to differentiate into more mature cells. Many progenitor cells differentiate along a single lineage, but may have quite extensive proliferative capacity.

In particular embodiments, the media and methods contemplated herein are useful for increasing proliferation, culturing, manufacturing, and/or expanding mesodermal stem or progenitor cells. Illustrative examples of mesodermal stem or progenitor cells include, but are not limited to bone marrow stem or progenitor cells, umbilical cord stem or progenitor cells, adipose tissue derived stem or progenitor cells, hematopoietic stem or progenitor cells (HSPCs), mesenchymal stem or progenitor cells, muscle stem or progenitor cells, kidney stem or progenitor cells, osteoblast stem or progenitor cells, chondrocyte stem or progenitor cells, and the like.

In other embodiments, the media and methods contemplated herein are useful for increasing proliferation, culturing, manufacturing, and/or expanding one or more ectodermal stem or progenitor cells. Illustrative examples of ectodermal stem or progenitor cells include, but are not limited to neural stem or progenitor cells, retinal stem or progenitor cells, skin stem or progenitor cells, and the like.

In other embodiments, the media and methods contemplated herein are useful for increasing proliferation, culturing, manufacturing, and/or expanding one or more endodermal stem or progenitor cells. Illustrative examples of endodermal stem or progenitor cells include, but are not limited to liver stem or progenitor cells, pancreatic stem or progenitor cells, epithelial stem or progenitor cells, and the like.

In certain embodiments the media and methods contemplated herein are useful for increasing proliferation, culturing, manufacturing, and/or expanding one or more of a bone cell, osteocyte, osteoblast, adipose cell, chondrocyte, chondroblast, muscle cell, skeletal muscle cell, myoblast, myocyte, smooth muscle cell, bladder cell, bone marrow cell, central nervous system (CNS) cell, peripheral nervous system (PNS) cell, glial cell, astrocyte cell, neuron, pigment cell, epithelial cell, skin cell, endothelial cell, vascular endothelial cell, breast cell, colon cell, esophagus cell, gastrointestinal cell, stomach cell, colon cell, head cell, neck cell, gum cell, tongue cell, kidney cell, liver cell, lung cell, nasopharynx cell, ovary cell, follicular cell, cervical cell, vaginal cell, uterine cell, pancreatic cell, pancreatic parenchymal cell, pancreatic duct cell, pancreatic islet cell, prostate cell, penile cell, gonadal cell, testis cell, hematopoietic cell, lymphoid cell, or myeloid cell.

In a preferred embodiment, the media and methods contemplated herein are useful for increasing proliferation, culturing, manufacturing, and/or expanding a population of hematopoietic cells, e.g., hematopoietic stem cells, hematopoietic progenitor cells, immune effector cells, T cells, NKT cells, NK cells and the like. Illustrative sources to obtain hematopoietic cells include, but are not limited to: cord blood, bone marrow, mobilized peripheral blood mononuclear cells, lymph nodes tissue, thymus tissue, tissue from a site of infection, ascites, pleural effusion, spleen tissue, and tumors.

Hematopoietic stem cells (HSCs) give rise to committed hematopoietic progenitor cells (HPCs) that are capable of generating the entire repertoire of mature blood cells over the lifetime of an organism. The term "hematopoietic stem cell" or "HSC" refers to multipotent stem cells that give rise to the all the blood cell types of an organism, including myeloid (e.g., monocytes and macrophages, neutrophils, basophils, eosinophils, erythrocytes, megakaryocytes/platelets, dendritic cells), and lymphoid lineages (e.g., T-cells, B-cells, NK-cells), and others known in the art (See Fei, R., et al., U.S. Pat. No. 5,635,387; McGlave, et al., U.S. Pat. No. 5,460,964; Simmons, P., et al., U.S. Pat. No. 5,677,136; Tsukamoto, et al., U.S. Pat. No. 5,750,397; Schwartz, et al., U.S. Pat. No. 5,759,793; DiGuisto, et al., U.S. Pat. No. 5,681,599; Tsukamoto, et al., U.S. Pat. No. 5,716,827). When transplanted into lethally irradiated animals or humans, hematopoietic stem and progenitor cells can repopulate the erythroid, neutrophil-macrophage, megakaryocyte and lymphoid hematopoietic cell pool.

Additional illustrative examples of hematopoietic stem or progenitor cells suitable for use with media and methods contemplated herein include hematopoietic cells that are $CD34^+CD38^{Lo}CD90^+CD45^{RA-}$, hematopoietic cells that are $CD34^+$, $CD59^+$, $Thy1/CD90^+$, $CD38^{Lo/-}$, $C-kit/CD117^+$, and $Lin^{(-)}$, hematopoietic cells that are $CD34^+$, and hematopoietic cells that are $CD133^+$. In a preferred embodiment, a population of cells comprises hematopoietic cells that are $CD133^+CD90^+$, $CD133^+CD34^+$, or $CD133^+CD90^+CD34^+$.

In particular embodiments, the media and methods contemplated herein are useful for increasing proliferation, culturing, manufacturing, and/or expanding a population of hematopoietic stem and/or progenitor cells that has been, or that will be, genetically modified to express a therapeutic protein and/or used in a gene therapy. As used herein, the term "genetically modified" or "genetically engineered" refers to the chromosomal or extrachromosomal addition of extra genetic material in the form of DNA or RNA to the total genetic material in a cell. Genetic modifications may be targeted or non-targeted to a particular site in a cell's genome. In one embodiment, genetic modification is site-specific. In one embodiment, genetic modification is not site-specific. As used herein, the term "gene therapy" refers to the introduction of extra genetic material in the form of DNA or RNA into the total genetic material in a cell that restores, corrects, or modifies expression of a gene.

In one embodiment, a population of hematopoietic stem and/or progenitor cells is genetically modified with a viral vector, e.g., a lentiviral vector, encoding a therapeutic protein selected from the group consisting of: a globin, a human globin, a human β-globin, a human δ-globin, a human γ-globin, a human anti-sickling β-globin, or a human $β^{A-T87Q}$-globin, a human $β^{A-G16D/E22A/T87Q}$-globin, and a human $β^{A-T87Q/K95E/K120E}$-globin.

In various embodiments, the hematopoietic cell is an immune effector cell. An "immune effector cell," is any cell of the immune system that has one or more effector functions (e.g., cytotoxic cell killing activity, secretion of cytokines, induction of ADCC and/or CDC). Illustrative immune effector cells contemplated in particular embodiments are T lymphocytes, in particular cytotoxic T cells (CTLs; CD8+ T cells), TILs, and helper T cells (HTLs; CD4+ T cells). In one embodiment, immune effector cells include natural killer (NK) cells. In one embodiment, immune effector cells include natural killer T (NKT) cells. In yet other embodiments, the immune effector cells include regulatory T cells and/or dendritic cells.

The terms "T cell" or "T lymphocyte" are art-recognized and are intended to include thymocytes, naïve T lymphocytes, immature T lymphocytes, mature T lymphocytes, resting T lymphocytes, or activated T lymphocytes. A T cell can be a T helper (Th) cell, for example a T helper 1 (Th1) or a T helper 2 (Th2) cell. The T cell can be a helper T cell (HTL; CD4+ T cell) CD4+ T cell, a cytotoxic T cell (CTL; CD8+ T cell), a tumor infiltrating cytotoxic T cell (TIL; CD8+ T cell), CD4+CD8+ T cell, CD4-CD8- T cell, or any other subset of T cells. In one embodiment, the T cell is an NKT cell. Other illustrative populations of T cells suitable for use in particular embodiments include naïve T cells and memory T cells.

In particular embodiments, the media and methods contemplated herein are useful for increasing proliferation, culturing, manufacturing, and/or expanding a population of immune effector cells that has been, or that will be, genetically modified to express a therapeutic protein, e.g., an engineered antigen receptor. In one embodiment, a population of immune effector cells is genetically modified with a viral vector, e.g., a lentiviral vector, encoding a therapeutic protein selected from the group consisting of an engineered αβ TCR, an engineered γδ TCR, a dimerizing agent regulated immunoreceptor complex (DARIC), a chimeric antigen receptor (CAR), a bispecific T cell engager (BiTE), and zetakine receptor. In particular embodiments, the therapeutic protein is an engineered antigen receptor that binds a target antigen selected from the group consisting of: alpha folate receptor (FRα), $\alpha_v\beta_6$ integrin, B cell maturation antigen (BCMA), B7-H3 (CD276), B7-H6, carbonic anhydrase IX (CAIX), CD16, CD19, CD20, CD22, CD30, CD33, CD37, CD38, CD44, CD44v6, CD44v7/8, CD70, CD79a, CD79b, CD123, CD133, CD138, CD171, carcinoembryonic antigen (CEA), C-type lectin-like molecule-1 (CLL-1), CD2 subset 1 (CS-1), chondroitin sulfate proteoglycan 4 (CSPG4), cutaneous T cell lymphoma-associated antigen 1 (CTAGE1), epidermal growth factor receptor (EGFR), epidermal growth factor receptor variant III (EGFRvIII), epithelial glycoprotein 2 (EGP2), epithelial glycoprotein 40 (EGP40), epithelial cell adhesion molecule (EPCAM), ephrin type-A receptor 2 (EPHA2), fibroblast activation protein (FAP), Fc Receptor Like 5 (FCRL5), fetal acetylcholinesterase receptor (AchR), ganglioside G2 (GD2), ganglioside G3 (GD3), Glypican-3 (GPC3), EGFR family including ErbB2 (HER2), IL-11Rα, IL-13Rα2, Kappa, cancer/testis antigen 2 (LAGE-1A), Lambda, Lewis-Y (LeY), L1 cell adhesion molecule (L1-CAM), melanoma antigen gene (MAGE)-A1, MAGE-A3, MAGE-A4, MAGE-A6, MAGEA10, melanoma antigen recognized by T cells 1 (MelanA or MART1), Mesothelin (MSLN), MUC1, MUC16, neural cell adhesion molecule (NCAM), cancer/testis antigen 1 (NY-ESO-1), polysialic acid; placenta-specific 1 (PLAC1), preferentially expressed antigen in melanoma (PRAME), prostate stem cell antigen (PSCA), prostate-specific membrane antigen (PSMA), receptor tyrosine kinase-like orphan receptor 1 (ROR1), synovial sarcoma, X breakpoint 2 (SSX2), Survivin, tumor associated glycoprotein 72 (TAG72), tumor endothelial marker 1 (TEM1/CD248), tumor endothelial marker 7-related (TEM7R), trophoblast glycoprotein (TPBG), NKG2D ligands, vascular endothelial growth factor receptor 2 (VEGFR2), and Wilms tumor 1 (WT-1).

E. Genome Editing

The media and methods contemplated herein are useful for increasing proliferation, culturing, manufacturing, and/or expanding immune effector cells and/or hematopoietic stem or progenitor cells modified by genome editing.

As used herein, the term "genome editing" refers to the use of one or more nucleases to substitute, delete, and/or introduce of genetic material at a target site in the cell's genome, which restores, corrects, and/or modifies expression of a gene. Illustrative examples of nucleases that may be used for genome editing include, but are not limited to homing endonucleases (meganucleases), megaTALs, transcription activator-like effector nucleases (TALENs), zinc finger nucleases (ZFNs), ARCUS nucleases, and clustered regularly-interspaced short palindromic repeats (CRISPR)/Cas nuclease systems.

Genome editing contemplated in particular embodiments comprises introducing one or more engineered nucleases (or mRNA encoding the same) into a cell to generate DNA lesions at a target site in the cell's genome, optionally in the presence of a donor repair template.

Donor repair templates provide one or more polynucleotide sequences that can be incorporated into the genome at the target site through homologous recombination.

In various embodiments, the donor repair template comprises one or more polynucleotides encoding a gene or fragment thereof including, but not limited to: β globin, δ globin, γ globin, BCL11A, KLF1, CCR5, CXCR4, PPP1R12C (AAVS1), HPRT, albumin, Factor VIII, Factor IX, LRRK2, Htt, SOD1, C9orf72, TARDBP, FUS, RHO, CFTR, SFTPB, TRAC, TRBC, PD1, CTLA-4, HLA A, HLA B, HLA C, HLA-DP, HLA-DQ, HLA-DR, LMP7, TAP 1, TAP2, TAPBP, CIITA, DMD, GR, IL2RG, Rag-1, RFX5, FAD2, FAD3, ZP15, KASH, MDH, and EPSPS; a bispecific T cell engager (BiTE) molecule; a hormone; a cytokine (e.g., IL-2, insulin, IFN-γ, IL-7, IL-21, IL-10, IL-12, IL-15, and TNF-α), a chemokine (e.g., MIP-la, MIP-10, MCP-1, MCP-3, and RANTES), a cytotoxin (e.g., Perforin, Granzyme A, and Granzyme B), a cytokine receptor (e.g., an IL-2 receptor, an IL-7 receptor, an IL-12 receptor, an IL-15 receptor, and an IL-21 receptor), and an engineered antigen receptor (e.g., an engineered T cell receptor (TCR), a chimeric antigen receptor (CAR), a Daric receptor or components thereof, or a chimeric cytokine receptor). In various embodiments, the media and methods contemplated herein are useful for culturing, manufacturing, and/or expanding genetically modified immune effector cells and/or hematopoietic stem or progenitor cells comprising one or more genome edits. In some embodiments, cells comprising one or more genome edits have been transduced with a gene therapy vector. In some embodiments, the gene therapy vector comprises a polynucleotide encoding a therapeutic protein. In some embodiments, the gene therapy vector encodes a chimeric antigen receptor (CAR) or engineered T cell receptor (TCR).

Techniques for gene editing are generally known in the art.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Improved Culture Medium Increases Proliferation, Viability, and Desired Cellular Phenotypes For the purpose of culturing immune effector cells and/or hematopoietic stem or progenitor cells, the present inventors envisaged that by tightly controlling osmolarity within a physiological range and supplementing the cell medium with L-ornithine, one could increase cell proliferation while improving cellular phenotypes critical for efficacy of various cell-therapy treatments. Accordingly, the inventors formulated an improved medium comprising L-oithine having an osmolarity of about 310-320 mOsm/kg. The current medium (TCGM; osmolarity of about 330-340 mOsm/kg) and improved (PEM1) medium formulation used in the present study are outlined in Table 1.

TABLE 1

| Component | Manufacturer # or CAS # | Current Media Formulation (TCGM) Quantity [/L final media] | Improved Media Formulation (PEM1) Quantity [/kg final media] |
|---|---|---|---|
| X-VIVO ™ 15 w/o Gentamicin or Phenol Red | Lonza 04-744Q/08-879H | 930 mL/L | 820 mL/kg |
| GlutaMAX-I, 200 mM (100X) | Gibco 35050-061 | 10 mL/L | 10 mL/kg |
| HEPES Buffer Solution, 1M (100X) | Gibco 15630-080 | 10 mL/L | 10 mL/kg |
| HI Human AB Serum | Gemini 100-512, Valley Biomedical HP1022 | 50 mL/L | 50 mL/kg |
| Poloxamer 188, USP/EP grade | CAS 9003-11-6 | N/A | 1 g/kg |
| L-Ornithine HCl | CAS 3184-13-2 | N/A | 0.25 g/kg |
| $NaHCO_3$ | CAS 144-55-8 | N/A | 0.60 g/kg |
| NaCl | CAS 7647-14-5 | N/A | 0.15 g/kg |
| KCl | CAS 7447-40-7 | N/A | 0.03 g/kg |
| Water (milliQ/WFI) | CAS 7732-18-5 | N/A | 107.97 g/kg |
| rhIL-2 ($5 \times 10^5$ IU/mL) | Cellgenix 1420-050, 1020-1000 | 0.5 mL/L* (added post finalization) | 0.5 mL/kg* (added post finalization) |

In the present study, frozen peripheral blood mononuclear cells (PBMCs) isolated from two different human donors via leukapheresis were used as the source of T cells for manufacturing. PBMCs were thawed in a 37° C. water bath, transferred to a 50 mL conical tube containing warm TCGM media and centrifuged for approximately 10 minutes to pellet the cells. The supernatant was removed and cell pellet was resuspended in a small volume of TCGM containing 250 IU/mL recombinant human IL-2 to a density of approximately $1\times10^6$ nucleated cells/mL, with the targeted number of CD3+ PBMCs to be at least $0.3\times10^6$ cells/mL. T cell activation was induced by adding anti-CD3 and anti-CD28 antibodies at 50 ng/mL. Cultures were incubated in a 37° C., 5% $CO_2$ incubator for about 24 hours. (Day 0 to Day 1).

On Day 1, cells were transduced with lentivirus comprising a polynucleotide encoding a therapeutic CAR at a multiplicity of infection (MOI) of about 10 based on Day 0 PBMC count. The virus was diluted in TCGM+IL-2 and added as a 20% volume increase to the culture. Cells were allowed to incubate for about 36-48 hours (2 nominal days) until Day 3, where they were transferred to a rocking WAVE bioreactor until day 10. For these experiments, the improved media formulation (PEM1) was introduced on Day 3 and replaced use of TCGM throughout the rest of the expansion. In all embodiments, cell densities were targeted to $0.3$-$0.5\times 10^6$ cells/mL each nominal day until the final working volume was reached. At this point, perfusion with the custom media formulation was introduced at a minimum of 0.24 vessel volumes per day (vvd) to maintain nutrient supplementation and metabolite removal. Perfusion was continued through the end of culture with ranges between 0.24 to 1.0 vvd to maintain appropriate supplementation levels, as determined through daily sampling and monitoring of metabolites and cell densities.

Figure 2:
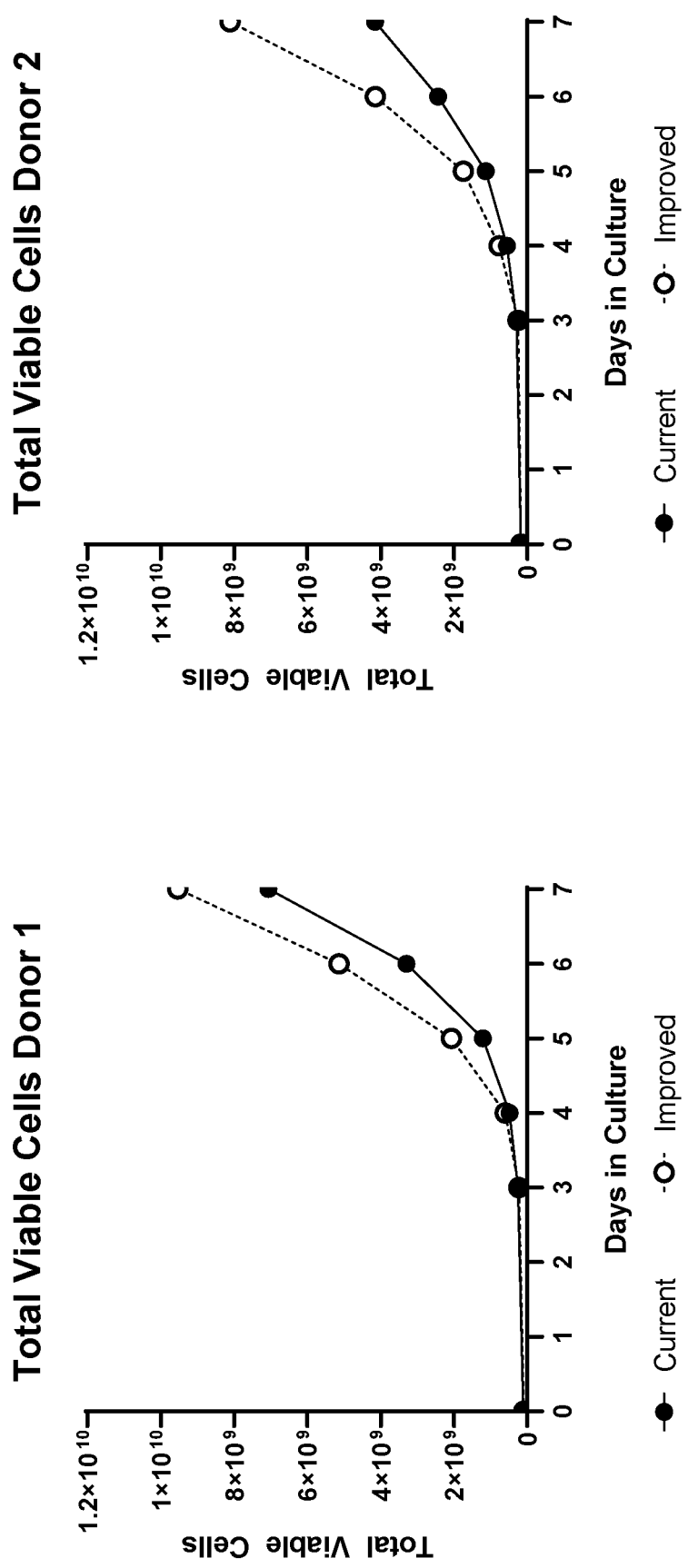
FIG. 2 is a graph showing total viable CAR-T cells cultured in current and improved medium formulations.

In one exemplary experimental run, cultures with the improved media formulation were able to attain at least one additional population doubling over the current formulation (FIG. 1) on Day 7 of culture expansion. In terms of viable cell concentrations, the total number of viable cells on Day 7 reached 9.54 billion versus 7.07 billion cells in one donor and 8.11 billion versus 4.16 billion in another donor with the improved vs current formulations, respectively (FIG. 2).

Figure 3:
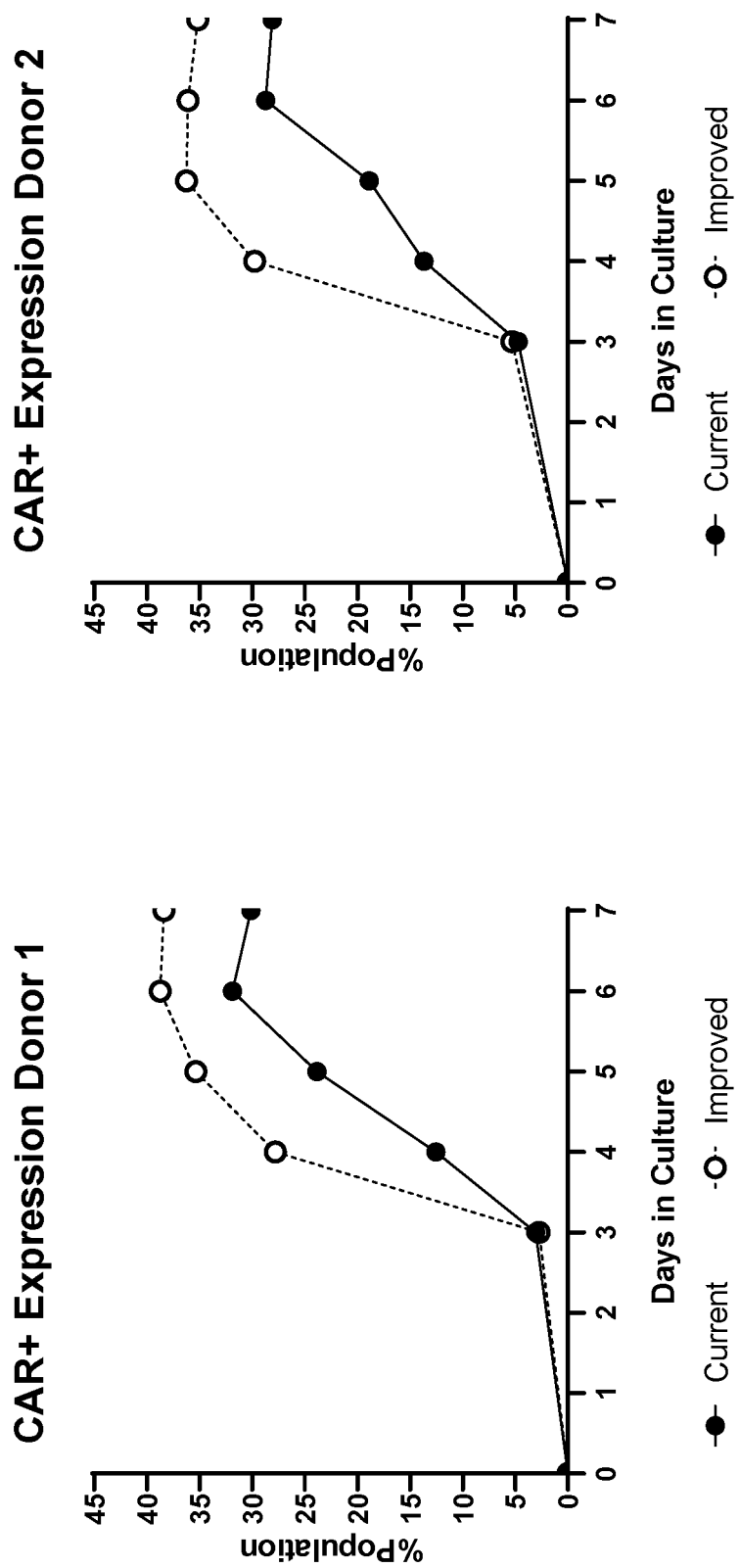
FIG. 3 is a graph showing the percent of T cells having CAR+ expression over time cultured in current and improved medium formulations.
Figure 4:
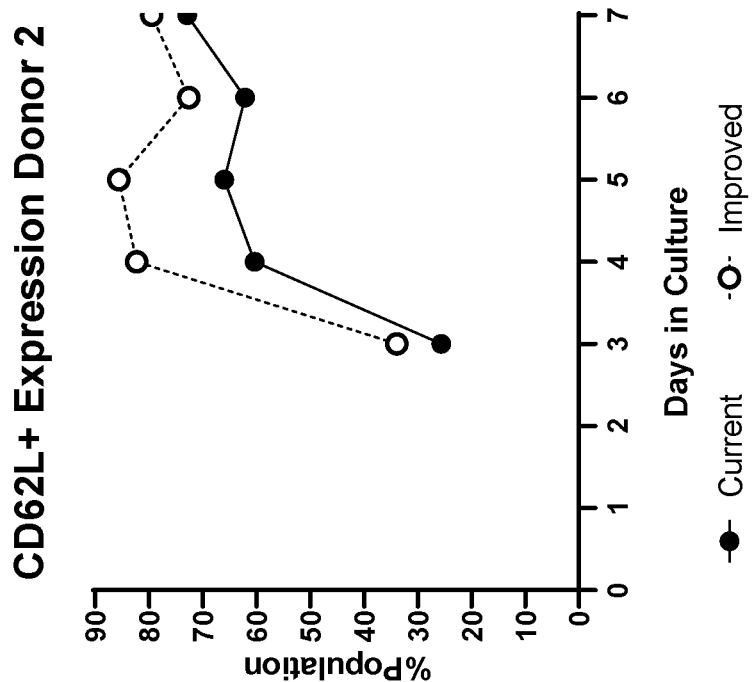
FIG. 4 is a graph showing the percent of T cells having CD62L+ expression cultured in current and improved medium formulations.
Figure 4:
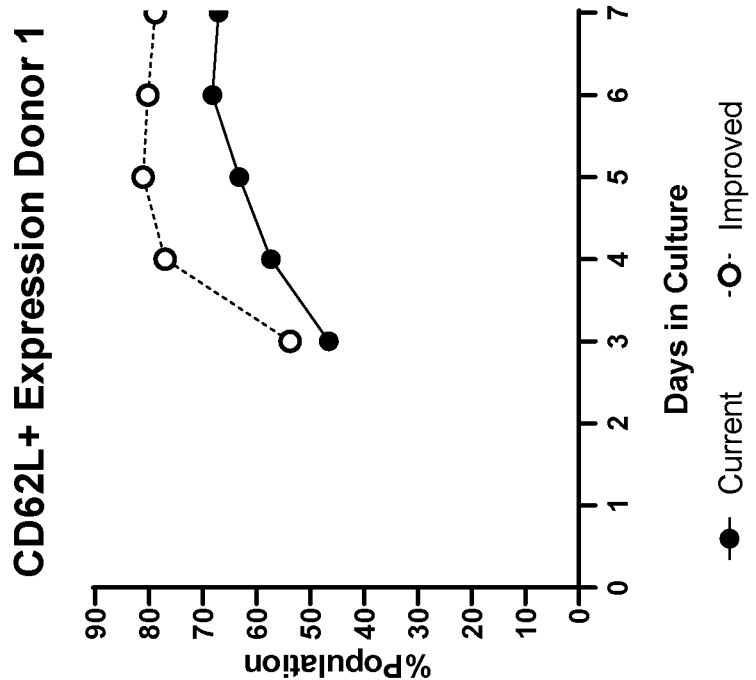
Figure 5:
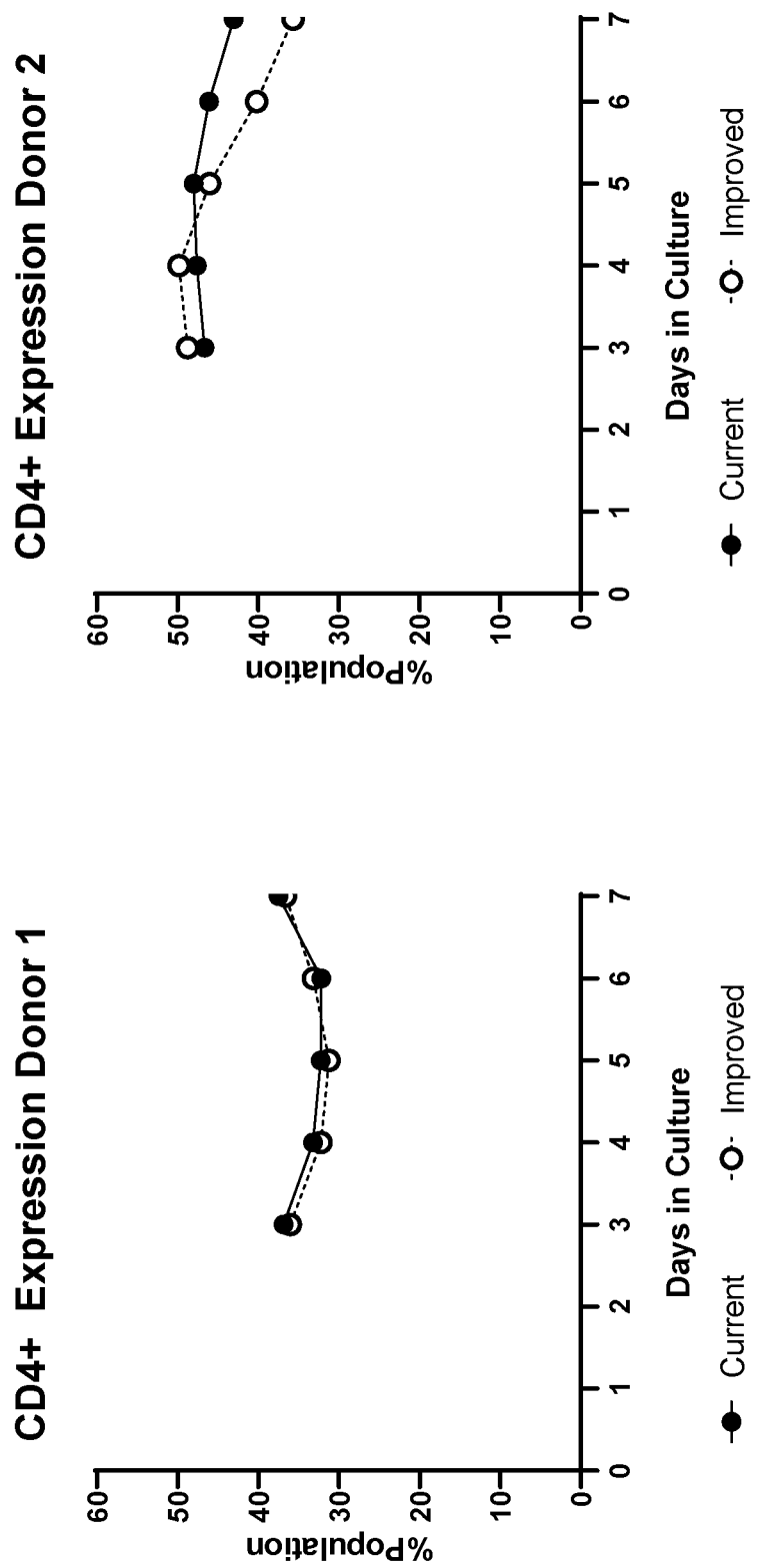
FIG. 5 is a graph showing the percent of CAR-T cells having CD4+ expression cultured in current and improved medium formulations.
Figure 6:
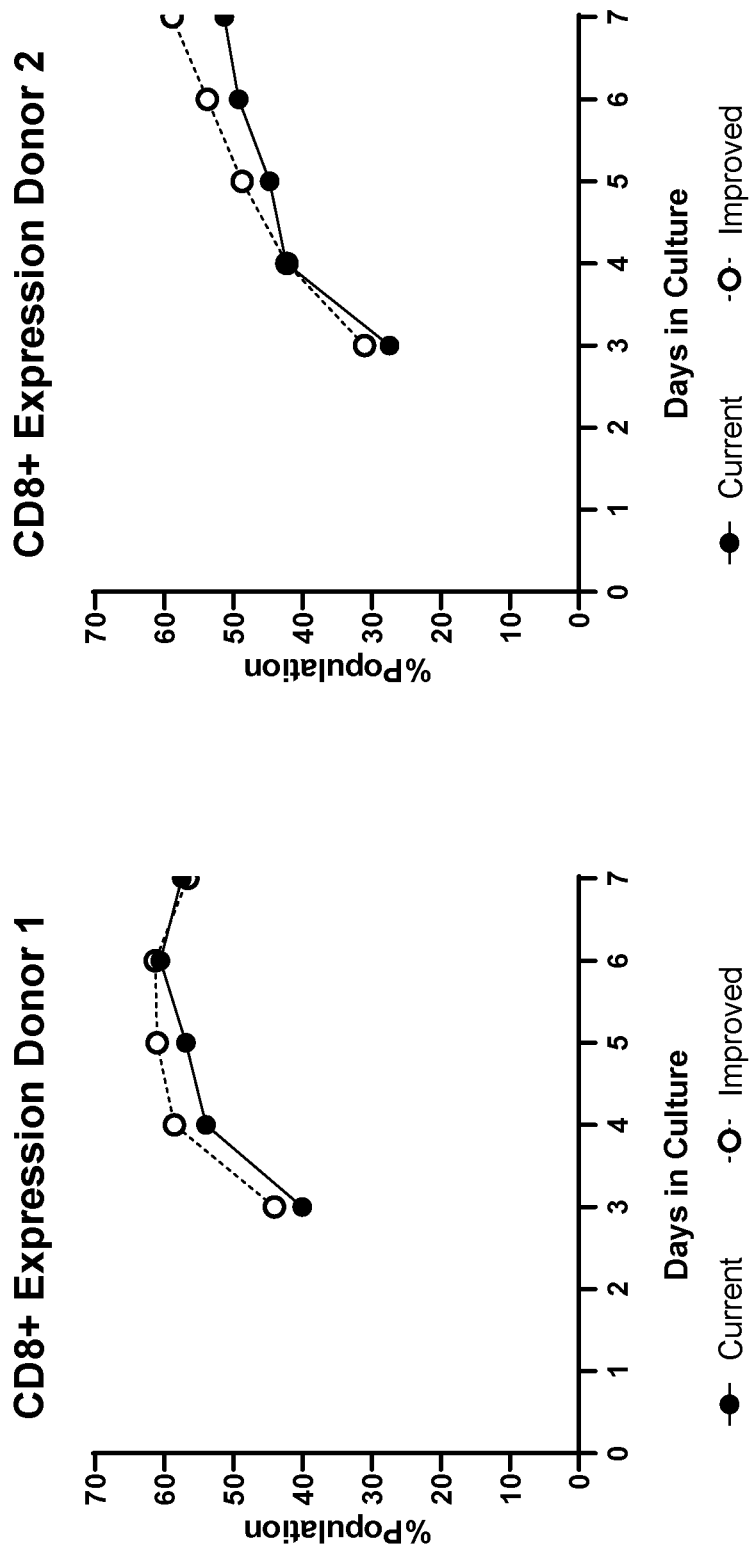
FIG. 6 is a graph showing the percent of CAR-T cells having CD8+ expression cultured in current and improved medium formulations.

Within 24 hours of use of the improved formulation, the percent of CAR+ cells increased significantly and were maintained in a higher percentage of the population through day 7 of the culture (FIG. 3). By day 7, the total number of CAR+ cells was 3.66 billion (38.4% of 9.54 billion) versus 2.13 billion (30.1% of 2.13 billion) in one donor, 2.85 billion (35.17% of 8.11 billion) versus 1.17 billion (28.11% of 4.16 billion) in another donor with the improved vs current formulations, respectively. This corresponds to an approximately 72% improvement in one donor and 144% improvement in the other donor for total CAR+ cell numbers. Increased and sustained memory T cell marker expression, tracked here through CD62L expression, was observed during the initial expansion of the cells in the improved formulation, (FIG. 4). CD4 and CD8 ratios were comparable between the current and improved formulations (FIG. 5 and FIG. 6).

In summary, the improved medium formulation was able to increase total CAR+ cell counts by approximately 35% to more than double over the current media used, in supporting growth and increased CAR+ population percentages. In addition, with increased growth and CAR+ expression, manufacturing time was decreased by at least a nominal day and still hit required dosing densities.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of manufacturing a population of immune effector cells or hematopoietic stem or progenitor cells (HSPCs), comprising culturing the immune effector cells or HSPCs in a culture medium comprising:
   a) a base medium for culturing immune effector cells or hematopoietic stem or progenitor cells (HSPCs),
   b) a buffer that maintains the pH of the culture medium in the range of about 6.5 to about 7.5,
   c) a serum or serum replacement,
   d) one or more mono- and di-valent salts selected from the group consisting of $CaCl_2$, NaCl, and KCl,
   e) a recombinant growth factor; and
   f) about 0.75 to about 3.0 mM L-ornithine;
   wherein the culture medium has an osmolality of about 275 mOsm/kg to about 320 mOsm/kg, and
   wherein cell proliferation is increased compared to immune effector cells or HSPCs grown in a culture medium without L-ornithine and/or an osmolality of about 275 mOsm/kg to about 320 mOsm/kg.

2. The method of claim 1, wherein cell viability is increased compared to cells grown in a culture medium without L-ornithine and/or an osmolality of about 275 mOsm/kg to about 320 mOsm/kg.

3. The method of claim 1, wherein CD62L+ expression is increased in the effector cells compared to immune effector cells grown in a culture medium without L-ornithine and/or an osmolality of about 275 mOsm/kg to about 320 mOsm/kg.

4. The method of claim 1, wherein the cells are genetically modified to express a therapeutic protein, and wherein the therapeutic protein expression is increased compared to genetically modified cells grown in a culture medium without L-ornithine and/or an osmolality of about 275 mOsm/kg to about 320 mOsm/kg.

5. The method of claim 1, wherein the cells are cultured at about 38° C. to about 39.5° C.

6. The method of claim 1, wherein the culture medium has an osmolality of about 310 mOsm/kg.

7. The method of claim 1, wherein the recombinant growth factor increases ornithine decarboxylase (ODC) expression and/or ODC activity in the immune effector cells or HSPCs as compared to immune effector cells or HSPCs grown in a culture media without L-ornithine.

8. The method of claim 7, wherein the recombinant growth factor is IL-2.

9. The method of claim 1, wherein:
   a) the one or more mono- and di-valent salts comprise NaCl and KCl, and wherein the culture medium comprises a final ratio of NaCl to KCl of about 20:1 to about 30:1;
   b) the culture medium comprises about 0.5 mM to about 3 mM $CaCl_2$); and/or
   c) the culture medium comprises about 0.40 g/kg to about 0.80 g/kg $NaHCO_3$.

10. The method of claim 1, wherein the culture medium comprises about 0.5 g/kg to about 1.5 g/kg poloxamer 188.

11. The method of claim 1, wherein the culture medium comprises about 5 mM to about 25 mM HEPES.

12. The method of claim 1, wherein the culture medium comprises about 40 g/kg to about 60 g/kg heat inactivated (HI) AB serum or gamma irradiated (GI) AB serum.

13. The method of claim 1, wherein the culture medium further comprises at least one of:
   a) at least one of recombinant growth factor or cytokine selected from the group consisting of GM-CSF, G-CSF, IFN-γ, TGFβ, and TNFα;
   b) human serum albumin (HSA);
   c) cholesterol; and
   d) vitamin E.

14. The method of claim 1, wherein the population of immune effector cells comprises cytotoxic T lymphocytes (CTLs), helper T cells, natural killer (NK) cells, natural killer T (NKT) cells, regulatory T cells, or dendritic cells.

15. The method of claim 1, wherein the population of hematopoietic stem or progenitor cells (HSPCs) comprise at least one of CD44+, CD34+, CD90+ or CD133+ cells.

16. The method of claim 1, wherein the one or more mono- and di-valent salts comprises NaCl and KCl, and
   wherein the final molar ratio of NaCl to KCl in the culture medium is about 20:1 to about 30:1.

17. The method of claim 1, wherein
   b) the buffer that maintains the pH of the culture medium is 10 mM HEPES buffer;
   c) the serum or serum replacement is about 50 mL/kg HI Human AB Serum or GI AB serum;
   d) the one or more mono- and di-valent salts are $CaCl_2$), NaCl, and KCl, wherein the medium comprises 1.89 mM $CaCl_2$), about 0.15 g/kg NaCl, and about 0.03 g/kg KC, wherein the final molar ratio of NaCl to KCl in the culture medium is about 28:1;
   e) wherein the recombinant growth factor is recombinant human IL-2 growth factor, and wherein the culture medium comprises about 250 IU/mL recombinant human IL-2 growth factor;
   f) wherein the medium comprises about 0.25 g/kg L-ornithine HCl;
   and wherein the culture medium further comprises about 0.60 g/kg $NaHCO_3$, about 1 g/kg poloxamer 188, and about 2 mM L-alanine-L-Glutamine dipeptide; and
   wherein the cell culture medium has an osmolality of about 310 mOsm/kg.

* * * * *